(12) United States Patent
Ramshaw et al.

(10) Patent No.: US 10,155,793 B2
(45) Date of Patent: Dec. 18, 2018

(54) MODIFIED BACTERIAL COLLAGEN-LIKE PROTEINS

(71) Applicant: Commonwealth Scientific and Industrial Research Organisation, Campbell, Australian Capital Territory (AU)

(72) Inventors: John Alan Maurice Ramshaw, Pascoe Vale (AU); Jerome Anthony Werkmeister, Camberwell (AU); Violet Stoichevska, Lower Templestowe (AU); Yong Yi Peng, Bulleen (AU)

(73) Assignee: Commonwealth Scientific and Industrial Research Organisation, Acton, ACT (AU)

( * ) Notice: Subject to any disclaimer, the term of this patent is extended or adjusted under 35 U.S.C. 154(b) by 0 days.

(21) Appl. No.: 15/024,290

(22) PCT Filed: Sep. 9, 2014

(86) PCT No.: PCT/AU2014/000885
§ 371 (c)(1),
(2) Date: Mar. 24, 2016

(87) PCT Pub. No.: WO2015/031950
PCT Pub. Date: Mar. 12, 2015

(65) Prior Publication Data
US 2016/0376326 A1    Dec. 29, 2016

(30) Foreign Application Priority Data
Sep. 9, 2013    (AU) ............................... 2013903444

(51) Int. Cl.
| | | |
|---|---|---|
| *C07K 14/195* | (2006.01) | |
| *A61K 8/65* | (2006.01) | |
| *C07K 14/78* | (2006.01) | |
| *A61Q 19/08* | (2006.01) | |
| *A61K 38/00* | (2006.01) | |

(52) U.S. Cl.
CPC .............. *C07K 14/195* (2013.01); *A61K 8/65* (2013.01); *A61Q 19/08* (2013.01); *C07K 14/78* (2013.01); *A61K 38/00* (2013.01); *A61K 2800/10* (2013.01)

(58) Field of Classification Search
None
See application file for complete search history.

(56) References Cited

FOREIGN PATENT DOCUMENTS

| | | |
|---|---|---|
| CN | 1793177 | 6/2008 |
| WO | 199310231 | 5/1993 |
| WO | 2010091251 | 8/2010 |
| WO | WO-2010091251 A2 * | 8/2010 ............. C07K 14/78 |
| WO | 2011008303 | 1/2011 |

OTHER PUBLICATIONS

Yu et al., "Dissecting a Bacterial Collagen Domain from *Streptococcus pyogenes*", The Journal of Biological Chemistry, 2011, pp. 18960-18968 (Year: 2011).*
Bai, H. et al, "Fabrication of Au Nanowires of Uniform Length and Diameter Using a Monodisperse and Rigid Biomolecular Template: Collagen-like Triple Helix", Angew. Chem. Int. Ed., 2007, 46:3319-3322.
Peng, Y. Y. et al, "Towards scalable production of a collagen-like protein from *Streptococcus pyogenes* for biomedical applications", Microbial Cell Factories, 2012, 11(146):1-8.

* cited by examiner

*Primary Examiner* — Lianko G Garyu
(74) *Attorney, Agent, or Firm* — Carol L. Francis; Bozicevic, Field & Francis LLP

(57) ABSTRACT

The present disclosure relates to recombinant or synthetic collagen-like proteins comprising at least one triple-helical domain and wherein the collagen-like protein is modified compared to a native bacterial collagen-like sequence.

11 Claims, 8 Drawing Sheets
Specification includes a Sequence Listing.

SEQUENCE LISTING

<160> NUMBER OF SEQ ID NOS: 26

<210> SEQ ID NO 1
<211> LENGTH: 7
<212> TYPE: PRT
<213> ORGANISM: Homo sapiens

<400> SEQUENCE: 1

Leu Val Pro Arg Gly Ser Pro
1               5

<210> SEQ ID NO 2
<211> LENGTH: 999
<212> TYPE: DNA
<213> ORGANISM: Artificial Sequence
<220> FEATURE:
<223> OTHER INFORMATION: chemically synthesized bacterial collagen
      sequence

<400> SEQUENCE: 2

| | | | | | |
|---|---|---|---|---|---|
| atgaatcaca | aagtgcatat | gcatcaccat | caccatcacg | ctgatgaaca | agaagagaaa |  60 |
| gctaaagtta | gaactgaatt | aattcaagag | ttagctcagg | gactaggggg | tattgagaaa | 120 |
| aaaaatttc | caactctagg | tgatgaagat | ttagatcata | cttatatgac | aaagctatta | 180 |
| acatacctac | aggaacgaga | acaagctgag | aatagttggc | gaaaaagact | actaaagggt | 240 |
| atacaagatc | atgcccttga | tctggtgcca | cgcggtagtc | ccgggctgcc | agggcccaga | 300 |
| ggggaacaag | gaccaacagg | tccaaccgga | cctgctggtc | cacgaggtct | acaaggtcta | 360 |
| caaggtctac | aaggtgaaag | aggggaacaa | ggaccaacag | gtcccgctgg | tccacgaggt | 420 |
| ctacaaggtg | aaagagggga | caaggaccaa | caggtctcg | ctggtaaagc | cggtgaagct | 480 |
| ggagccaaag | gcgaaaccgg | ccccgctggt | ccacagggtc | cacgtggtga | acaaggcccg | 540 |
| caaggtcttc | caggtaaaga | tggtgaagct | ggtgctcaag | cccagcagg | tccaatgggt | 600 |
| cctgctggtg | agcgaggtga | aaaggagaa | cctggtaccc | aaggcgctaa | aggtgatcgc | 660 |
| ggtgaaaccg | gtccagtagg | tccacgtggt | gagcgaggcg | aagccggtcc | cgctggaaaa | 720 |
| gatggtgaac | gtggtccagt | aggtccagct | ggtaaggacg | ccaaaacgg | ccaagatggt | 780 |
| cttccaggta | agacggtaa | ggacggccaa | acggtaaag | atggtcttcc | aggtaaagac | 840 |
| ggtaaggacg | ccaaaacgg | taagatggt | cttccaggta | aagacggtaa | ggacggtcaa | 900 |
| gatggtaaag | acggcctccc | aggtaaagac | ggtaaagatg | gcctcccagg | taaggacggt | 960 |
| aaggacggtc | aaccaggtaa | accgggtaaa | tattaagga | | | 999 |

<210> SEQ ID NO 3
<211> LENGTH: 331
<212> TYPE: PRT
<213> ORGANISM: Artificial Sequence
<220> FEATURE:
<223> OTHER INFORMATION: chemically synthesized bacterial collagen
      sequence

<400> SEQUENCE: 3

Met Asn His Lys Val His Met His His His His His Ala Asp Glu
1               5                   10                  15

Gln Glu Glu Lys Ala Lys Val Arg Thr Glu Leu Ile Gln Glu Leu Ala
                20                  25                  30

Gln Gly Leu Gly Gly Ile Glu Lys Lys Asn Phe Pro Thr Leu Gly Asp
            35                  40                  45

Glu Asp Leu Asp His Thr Tyr Met Thr Lys Leu Leu Thr Tyr Leu Gln
        50                  55                  60

Glu Arg Glu Gln Ala Glu Asn Ser Trp Arg Lys Arg Leu Leu Lys Gly
65                  70                  75                  80

Ile Gln Asp His Ala Leu Asp Leu Val Pro Arg Gly Ser Pro Gly Leu
                85                  90                  95

```
Pro Gly Pro Arg Gly Glu Gln Gly Pro Thr Gly Thr Gly Pro Ala
            100                 105                 110
Gly Pro Arg Gly Leu Gln Gly Leu Gln Gly Leu Gln Gly Glu Arg Gly
        115                 120                 125
Glu Gln Gly Pro Thr Gly Pro Ala Gly Pro Arg Gly Leu Gln Gly Glu
    130                 135                 140
Arg Gly Glu Gln Gly Pro Thr Gly Leu Ala Gly Lys Ala Gly Glu Ala
145                 150                 155                 160
Gly Ala Lys Gly Glu Thr Gly Pro Ala Gly Pro Gln Gly Pro Arg Gly
                165                 170                 175
Glu Gln Gly Pro Gln Gly Leu Pro Gly Lys Asp Gly Glu Ala Gly Ala
            180                 185                 190
Gln Gly Pro Ala Gly Pro Met Gly Pro Ala Gly Glu Arg Gly Glu Lys
        195                 200                 205
Gly Glu Pro Gly Thr Gln Gly Ala Lys Gly Asp Arg Gly Glu Thr Gly
    210                 215                 220
Pro Val Gly Pro Arg Gly Glu Arg Gly Glu Ala Gly Pro Ala Gly Lys
225                 230                 235                 240
Asp Gly Glu Arg Gly Pro Val Gly Pro Ala Gly Lys Asp Gly Gln Asn
                245                 250                 255
Gly Gln Asp Gly Leu Pro Gly Lys Asp Gly Lys Asp Gly Gln Asn Gly
            260                 265                 270
Lys Asp Gly Leu Pro Gly Lys Asp Gly Lys Asp Gly Gln Asn Gly Lys
        275                 280                 285
Asp Gly Leu Pro Gly Lys Asp Gly Lys Asp Gly Gln Asp Gly Lys Asp
    290                 295                 300
Gly Leu Pro Gly Lys Asp Gly Lys Asp Gly Leu Pro Gly Lys Asp Gly
305                 310                 315                 320
Lys Asp Gly Gln Pro Gly Lys Pro Gly Lys Tyr
                325                 330

<210> SEQ ID NO 4
<211> LENGTH: 1026
<212> TYPE: DNA
<213> ORGANISM: Artificial Sequence
<220> FEATURE:
<223> OTHER INFORMATION: chemically synthesized bacterial collagen
      sequence

<400> SEQUENCE: 4
atgggatgtc ccggcccggc gggcccggcg ggcccgcagg gcccggcggg cccggcgggc      60
gcgcagggcc cggcgggccc ggcgggcccg cagggcccgg cgggcccgca gggcagcgcg     120
ggcgcgcagg gcccgaaagg cgataccggc gcggcgggcc cggcgggcga agcgggcccg     180
aaaggcgaaa ccggcgcggc gggcccgaaa ggcgataccg gcgcggcggg cccggcgggc     240
ccgaaaggcg ataccggcgc ggcgggcccg cgggcccga aggcgatac cggcgcggcg     300 ggcgcgaccg gcccgaaagg cgaaaaaggc gaaaccggcg cggcgggccc gaaaggcgat     360
aaaggcgaaa ccggcgcggc gggcccgaaa ggcgataaag gcgaaaccgg cgcggcgggc     420
ccgaaaggcg aaaaaggcga aaccggcgcg gtgggcccga aaggcgataa aggcgaaacc     480
ggcgcggcgg gcccgaaagg cgatcgcggc gaaaccggcg cggtgggccc gaaaggcgat     540
aaaggcgaaa ccggcgcggt gggcccgaaa ggcgataaag gcgaaaccgg cgcgattggc     600
ccgaaaggcg ataaaggcga taaaggcgat aaaggcgatg cgggcgtggc gggcccgcag     660
ggcattcagg gcgtgaaagg cgataccggc ctgcagggcc cgaaaggcga tgcgggcccg     720
```

```
cagggcgcgc cgggcaccccc gggcggcccg agcattgaac aggtgatgcc gtggctgcat      780 ctgattttg atgcgtatga agattataaa gcgcagcgcg cgcgcgaagc gcgcgaactg       840
gaagaacgcc tggcggcgga agcgctggaa caggcggcgc gcgaagcggc ggaacgcgaa      900
gtggcggcgg cgattgaagc ggcgaacgcg gaagcgaaaa ttatgctgga tgatgaaacc      960
catgcggaag gcggcaaaaa aaaaaaaaaa cgcaaacata aagatcacca ccatcaccat     1020
cattaa                                                                1026
```

<210> SEQ ID NO 5
<211> LENGTH: 341
<212> TYPE: PRT
<213> ORGANISM: Artificial Sequence
<220> FEATURE:
<223> OTHER INFORMATION: chemically synthesized bacterial collagen
      sequence <400> SEQUENCE: 5

```
Met Gly Cys Pro Gly Pro Ala Gly Pro Ala Gly Pro Gln Gly Pro Ala
1               5                   10                  15

Gly Pro Ala Gly Ala Gln Gly Pro Ala Gly Pro Ala Gly Pro Gln Gly
            20                  25                  30

Pro Ala Gly Pro Gln Gly Ser Ala Gly Ala Gln Gly Pro Lys Gly Asp
        35                  40                  45

Thr Gly Ala Ala Gly Pro Ala Gly Glu Ala Gly Pro Lys Gly Glu Thr
    50                  55                  60

Gly Ala Ala Gly Pro Lys Gly Asp Thr Gly Ala Ala Gly Pro Ala Gly
65                  70                  75                  80

Pro Lys Gly Asp Thr Gly Ala Ala Gly Pro Ala Gly Pro Lys Gly Asp
                85                  90                  95

Thr Gly Ala Ala Gly Pro Lys Gly Asp Thr Gly Ala Ala Gly Pro Ala
            100                 105                 110

Gly Pro Lys Gly Asp Thr Gly Ala Ala Gly Pro Ala Gly Pro Lys Gly
        115                 120                 125

Asp Thr Gly Ala Ala Gly Glu Thr Gly Ala Ala Gly Pro Lys Gly Glu
    130                 135                 140

Lys Gly Glu Thr Gly Ala Val Gly Pro Lys Gly Asp Lys Gly Glu Thr
145                 150                 155                 160

Gly Ala Ala Gly Pro Lys Gly Asp Arg Gly Glu Thr Gly Ala Val Gly
                165                 170                 175

Pro Lys Gly Asp Lys Gly Glu Thr Gly Ala Val Gly Pro Lys Gly Asp
            180                 185                 190

Lys Gly Glu Thr Gly Ala Ile Gly Pro Lys Gly Asp Lys Gly Asp Lys
        195                 200                 205

Gly Asp Lys Gly Asp Ala Gly Val Ala Gly Pro Gln Gly Ile Gln Gly
    210                 215                 220

Val Lys Gly Asp Thr Gly Leu Gln Gly Pro Lys Gly Asp Ala Gly Pro
225                 230                 235                 240

Gln Gly Ala Pro Gly Thr Pro Gly Gly Pro Ser Ile Glu Gln Val Met
                245                 250                 255

Pro Trp Leu His Leu Ile Phe Asp Ala Tyr Glu Asp Tyr Lys Ala Gln
            260                 265                 270

Arg Ala Arg Glu Ala Arg Glu Leu Glu Glu Arg Leu Ala Ala Glu Ala
        275                 280                 285

Leu Glu Gln Ala Ala Arg Glu Ala Ala Glu Arg Glu Val Ala Ala Ala
    290                 295                 300
```

```
Ile Glu Ala Ala Asn Ala Glu Ala Glu Ile Met Leu Asp Asp Glu Thr
305                 310                 315                 320

His Ala Glu Gly Gly Lys Lys Lys Lys Arg Lys His Lys Asp His
            325                 330                 335

His His His His His
            340

<210> SEQ ID NO 6
<211> LENGTH: 999
<212> TYPE: DNA
<213> ORGANISM: Artificial Sequence
<220> FEATURE:
<223> OTHER INFORMATION: chemically synthesized bacterial collagen
      sequence

<400> SEQUENCE: 6
atgaatcaca aagtgcatat gcatcaccat caccatcacg ctgatgaaca agaagagaaa        60
gctaaagtta gaactgaatt aattcaagag ttagctcagg gactaggggg tattgagaaa       120 aaaaatttc caactctagg tgatgaagat ttagatcata cttatatgac aaagctatta       180 acataccta caggaacgaga acaagctgag aatagttggc gaaaaagact actaaagggt       240
atacaagatc atgcccttga tctggtgcca cgcggtagtc ccgggctgcc agggcccaga       300
ggggaacaag gaccaacagg tccaaccgga cctgctggtc acgaggtct acaaggtcta       360 caaggtctac aaggtgaaag aggggaacaa ggaccaacag gtcccgctgg tccacgaggt       420
ctacaaggtg aaagagggga acaaggacca acaggtctcg ctggtaaagc cggtgaagct       480
ggagccaaag gcgaaaccgg ccccgctggt ccacagggtc acgtggtga acaaggcccg       540 caaggtcttc aggtaaaga tggtgaagct ggtgctcaag cccagcagg tccaatgggt       600 cctgctggtg agcgaggtga aaaggagaa cctggtaccc aaggcgctaa aggtgatcgc       660
ggtgaaaccg gtccagtagg tccacgtggt gagcgaggcg aagccggtcc cgctggaaaa       720
gatggtgaac gtggtccagt aggtccagct ggtaaggacg ccaaaacgg ccaagatggt       780 cttccaggta agacggtaa ggacggccaa acggtaaag atggtcttcc aggtaaagac       840
ggtaaggacg ccaaaacgg taagatggt cttccaggta agacggtaa ggacggtcaa       900 gatggtaaag acggcctccc aggtaaagac ggtaaagatg gcctcccagg taaggacggt       960
aaggacggtc aaccaggtaa accggggtat gctaagga                              999

<210> SEQ ID NO 7
<211> LENGTH: 331
<212> TYPE: PRT
<213> ORGANISM: Artificial Sequence
<220> FEATURE:
<223> OTHER INFORMATION: chemically synthesized bacterial collagen
      sequence

<400> SEQUENCE: 7

Met Asn His Lys Val His Met His His His His His Ala Asp Glu
1               5                   10                  15

Gln Glu Glu Lys Ala Lys Val Arg Thr Glu Leu Ile Gln Glu Leu Ala
                20                  25                  30

Gln Gly Leu Gly Gly Ile Glu Lys Lys Asn Phe Pro Thr Leu Gly Asp
            35                  40                  45

Glu Asp Leu Asp His Thr Tyr Met Thr Lys Leu Leu Thr Tyr Leu Gln
        50                  55                  60

Glu Arg Glu Gln Ala Glu Asn Ser Trp Arg Lys Arg Leu Leu Lys Gly
65                  70                  75                  80
```

Ile Gln Asp His Ala Leu Asp Leu Val Pro Arg Gly Ser Pro Gly Leu
             85                  90                  95

Pro Gly Pro Arg Gly Glu Gln Gly Pro Thr Gly Pro Thr Gly Pro Ala
        100                 105                 110

Gly Pro Arg Gly Leu Gln Gly Leu Gln Gly Leu Gln Gly Glu Arg Gly
    115                 120                 125

Glu Gln Gly Pro Thr Gly Pro Ala Gly Pro Arg Gly Leu Gln Gly Glu
130                 135                 140

Arg Gly Glu Gln Gly Pro Thr Gly Leu Ala Gly Lys Ala Gly Glu Ala
145                 150                 155                 160

Gly Ala Lys Gly Glu Thr Gly Pro Ala Gly Pro Gln Gly Pro Arg Gly
            165                 170                 175

Glu Gln Gly Pro Gln Gly Leu Pro Gly Lys Asp Gly Glu Ala Gly Ala
        180                 185                 190

Gln Gly Pro Ala Gly Pro Met Gly Pro Ala Gly Glu Arg Gly Glu Lys
    195                 200                 205

Gly Glu Pro Gly Thr Gln Gly Ala Lys Gly Asp Arg Gly Glu Thr Gly
210                 215                 220

Pro Val Gly Pro Arg Gly Glu Arg Gly Glu Ala Gly Pro Ala Gly Lys
225                 230                 235                 240

Asp Gly Glu Arg Gly Pro Val Gly Pro Ala Gly Lys Asp Gly Gln Asn
            245                 250                 255

Gly Gln Asp Gly Leu Pro Gly Lys Asp Gly Lys Asp Gly Gln Asn Gly
        260                 265                 270

Lys Asp Gly Leu Pro Gly Lys Asp Gly Lys Asp Gly Gln Asn Gly Lys
    275                 280                 285

Asp Gly Leu Pro Gly Lys Asp Gly Lys Asp Gly Gln Asp Gly Lys Asp
290                 295                 300

Gly Leu Pro Gly Lys Asp Gly Lys Asp Gly Leu Pro Gly Lys Asp Gly
305                 310                 315                 320

Lys Asp Gly Gln Pro Gly Lys Pro Gly Tyr Cys
            325                 330

<210> SEQ ID NO 8
<211> LENGTH: 6
<212> TYPE: PRT
<213> ORGANISM: Artificial Sequence
<220> FEATURE:
<223> OTHER INFORMATION: chemically synthesized sequence

<400> SEQUENCE: 8

Gly Cys Cys Gly Lys Tyr
1               5

<210> SEQ ID NO 9
<211> LENGTH: 945
<212> TYPE: DNA
<213> ORGANISM: Artificial Sequence
<220> FEATURE:
<223> OTHER INFORMATION: chemically synthesized bacterial collagen
      sequence

<400> SEQUENCE: 9
atggatgaac aagaagaaaa agccaaagtt cgcaccgaac tgattcaaga actggcacag      60
ggtctgggtg gttttgagaa aaaaaacttt ccgaccctgg gtgatgaaga tctggatcat     120
acctatatga ccaaactgct gacctatctg caagaacgtg aacaggcaga aaatagctgg     180
cgtaaacgtc tgctgaaagg tattcaggat catgcactgg atcgtggcac cggtccgcgt     240

```
ggtgaacagg gtccgacagg tcctacaggt ccggcaggac cgcgtggtct gcagggtctg      300
caaggcctgc agggtgaacg cggtgagcag ggtcctaccg gaccggctgg tcctcgcgga      360
ctgcaaggtg aacgtggcga acagggacca acgggtctgg caggtaaagc cggtgaagcg      420
ggtgcaaaag gtgaaacggg tcctgccggt ccgcagggtc cacgcggtga acaaggacct      480
cagggtctgc ctggtaaaga tggcgaagcc ggtgcccagg gaccggcagg tccaatgggt      540
ccggctggcg aacgtggtga aaaaggcgaa ccgggtacac agggtgccaa aggcgatcgc      600
ggtgaaacag gtccggttgg tcctcgtggt gagcgtggtg aagccggtcc tgcaggcaaa      660
gatggggaac gtggtccggt gggtccagcc ggaaaagatg gtcagaatgg tcaggatggc      720
ctgccaggta agacgggaa agatggccag aacggcaaag acggtctgcc agggaaagat      780
ggtaaagacg gacaaaatgg caaagatggc ctgcctggca agatggaaa agacggtcag      840 gacggtaaag acgggctgcc tggaaaagac ggcaaagatg gactgcctgg taaagacggt      900
aaagatggtc aaccgggtaa acccggttgt tgtggcaaat attta                     945
```

<210> SEQ ID NO 10
<211> LENGTH: 314
<212> TYPE: PRT
<213> ORGANISM: Artificial Sequence
<220> FEATURE:
<223> OTHER INFORMATION: chemically synthesized bacterial collagen sequence

<400> SEQUENCE: 10

```
Met Asp Glu Gln Glu Glu Lys Ala Lys Val Arg Thr Glu Leu Ile Gln
1               5                   10                  15

Glu Leu Ala Gln Gly Leu Gly Gly Phe Glu Lys Lys Asn Phe Pro Thr
            20                  25                  30

Leu Gly Asp Glu Asp Leu Asp His Thr Tyr Met Thr Lys Leu Leu Thr
        35                  40                  45

Tyr Leu Gln Glu Arg Glu Gln Ala Glu Asn Ser Trp Arg Lys Arg Leu
    50                  55                  60

Leu Lys Gly Ile Gln Asp His Ala Leu Asp Arg Gly Thr Gly Pro Arg
65                  70                  75                  80

Gly Glu Gln Gly Pro Thr Gly Pro Thr Gly Pro Ala Gly Pro Arg Gly
                85                  90                  95

Leu Gln Gly Leu Gln Gly Leu Gln Gly Glu Arg Gly Glu Gln Gly Pro
            100                 105                 110

Thr Gly Pro Ala Gly Pro Arg Gly Leu Gln Gly Glu Arg Gly Glu Gln
        115                 120                 125

Gly Pro Thr Gly Leu Ala Gly Lys Ala Gly Glu Ala Gly Ala Lys Gly
    130                 135                 140

Glu Thr Gly Pro Ala Gly Pro Gln Gly Pro Arg Gly Glu Gln Gly Pro
145                 150                 155                 160

Gln Gly Leu Pro Gly Lys Asp Gly Glu Ala Gly Ala Gln Gly Pro Ala
                165                 170                 175

Gly Pro Met Gly Pro Ala Gly Glu Arg Gly Glu Lys Gly Glu Pro Gly
            180                 185                 190

Thr Gln Gly Ala Lys Gly Asp Arg Gly Glu Thr Gly Pro Val Gly Pro
        195                 200                 205

Arg Gly Glu Arg Gly Glu Ala Gly Pro Ala Gly Lys Asp Gly Glu Arg
    210                 215                 220

Gly Pro Val Gly Pro Ala Gly Lys Asp Gly Gln Asn Gly Gln Asp Gly
225                 230                 235                 240
```

Leu Pro Gly Lys Asp Gly Lys Asp Gly Gln Asn Gly Lys Asp Gly Leu
             245                 250                 255

Pro Gly Lys Asp Gly Lys Asp Gly Gln Asn Gly Lys Asp Gly Leu Pro
         260                 265                 270

Gly Lys Asp Gly Lys Asp Gly Gln Asp Gly Lys Asp Gly Leu Pro Gly
     275                 280                 285

Lys Asp Gly Lys Asp Gly Leu Pro Gly Lys Asp Gly Lys Asp Gly Gln
 290                 295                 300

Pro Gly Lys Pro Gly Cys Cys Gly Lys Tyr
305                 310

<210> SEQ ID NO 11
<211> LENGTH: 960
<212> TYPE: DNA
<213> ORGANISM: Artificial Sequence
<220> FEATURE:
<223> OTHER INFORMATION: chemically synthesized bacterial collagen
      sequence

<400> SEQUENCE: 11
atggctgatg aacaagaaga gaaagctaaa gttagaactg aattaattca agagttagct        60
cagggactag gggtattga gaaaaaaaat tttccaactc taggtgatga agatttagat       120
catacttata tgacaaagct attaacatac ctacaggaac gagaacaagc tgagaatagt       180
tggcgaaaaa gactactaaa gggtatacaa gatcatgccc ttgatcgtgg atgtcccggg       240
ctgccagggc ccagagggga caaggacca acaggtccaa ccggacctgc tggtccacga       300
ggtctacaag gtctacaagg tctacaaggt gaaagagggg aacaaggacc aacaggtccc       360
gctggtccac gaggtctaca aggtgaaaga ggggaacaag gaccaacagg tctcgctggt       420
aaagccggtg aagctggagc caaaggcgaa accggccccg ctggtccaca gggtccacgt       480
ggtgaacaag gcccgcaagg tcttccaggt aaagatggtg aagctggtgc tcaaggccca       540
gcaggtccaa tgggtcctgc tggtgagcga ggtgaaaaag gagaacctgg tacccaaggc       600
gctaaaggtg atcgcggtga accggtccaa gtaggtccac gtggtgagcg aggcgaagcc       660
ggtcccgctg gaaaagatgg tgaacgtggt ccagtaggtc cagctggtaa ggacggccaa       720
aacggccaag atggtcttcc aggtaaagac ggtaaggacg gccaaaacgg taaagatggt       780
cttccaggta agacggtaa ggacggccaa aacggtaaag atggtcttcc aggtaaagac       840
ggtaaggacg gtcaagatgg taagacggc ctcccaggta agacggtaa agatggcctc       900 ccaggtaagg acggtaagga cggtcaacca ggtaaaccgg gtattgcta aggatccgaa       960

<210> SEQ ID NO 12
<211> LENGTH: 316
<212> TYPE: PRT
<213> ORGANISM: Artificial Sequence
<220> FEATURE:
<223> OTHER INFORMATION: chemically synthesized bacterial collagen
      sequence

<400> SEQUENCE: 12

Met Ala Asp Glu Gln Glu Glu Lys Ala Lys Val Arg Thr Glu Leu Ile
1               5                  10                  15

Gln Glu Leu Ala Gln Gly Leu Gly Gly Ile Glu Lys Lys Asn Phe Pro
             20                 25                 30

Thr Leu Gly Asp Glu Asp Leu Asp His Thr Tyr Met Thr Lys Leu Leu
         35                 40                 45

Thr Tyr Leu Gln Glu Arg Glu Gln Ala Glu Asn Ser Trp Arg Lys Arg
    50                  55                  60

Leu Leu Lys Gly Ile Gln Asp His Ala Leu Asp Arg Gly Cys Pro Gly
 65                  70                  75                  80

Leu Pro Gly Pro Arg Gly Glu Gln Gly Pro Thr Gly Pro Thr Gly Pro
                 85                  90                  95

Ala Gly Pro Arg Gly Leu Gln Gly Leu Gln Gly Leu Gln Gly Glu Arg
            100                 105                 110

Gly Glu Gln Gly Pro Thr Gly Pro Ala Gly Pro Arg Gly Leu Gln Gly
        115                 120                 125

Glu Arg Gly Glu Gln Gly Pro Thr Gly Leu Ala Gly Lys Ala Gly Glu
130                 135                 140

Ala Gly Ala Lys Gly Glu Thr Gly Pro Ala Gly Pro Gln Gly Pro Arg
145                 150                 155                 160

Gly Glu Gln Gly Pro Gln Gly Leu Pro Gly Lys Asp Gly Glu Ala Gly
                165                 170                 175

Ala Gln Gly Pro Ala Gly Pro Met Gly Pro Ala Gly Glu Arg Gly Glu
            180                 185                 190

Lys Gly Glu Pro Gly Thr Gln Gly Ala Lys Gly Asp Arg Gly Glu Thr
        195                 200                 205

Gly Pro Val Gly Pro Arg Gly Glu Arg Gly Glu Ala Gly Pro Ala Gly
210                 215                 220

Lys Asp Gly Glu Arg Gly Pro Val Gly Pro Ala Gly Lys Asp Gly Gln
225                 230                 235                 240

Asn Gly Gln Asp Gly Leu Pro Gly Lys Asp Gly Lys Asp Gly Gln Asn
                245                 250                 255

Gly Lys Asp Gly Leu Pro Gly Lys Asp Gly Lys Asp Gly Gln Asn Gly
            260                 265                 270

Lys Asp Gly Leu Pro Gly Lys Asp Gly Lys Asp Gly Gln Asp Gly Lys
        275                 280                 285

Asp Gly Leu Pro Gly Lys Asp Gly Lys Asp Gly Leu Pro Gly Lys Asp
        290                 295                 300

Gly Lys Asp Gly Gln Pro Gly Lys Pro Gly Tyr Cys
305                 310                 315

<210> SEQ ID NO 13
<211> LENGTH: 975
<212> TYPE: DNA
<213> ORGANISM: Artificial Sequence
<220> FEATURE:
<223> OTHER INFORMATION: chemically synthesized bacterial collagen
      sequence

<400> SEQUENCE: 13
atgcatcacc atcaccatca cgatgaacaa gaagagaaag ctaaagttag aactgaatta      60
attcaagagt tagctcaggg actaggggt tttgagaaaa aaaattttcc aactctaggt     120
gatgaagatt tagatcatac ttatatgaca aagctattaa cataccctaca ggaacgagaa    180 caagctgaga atagttggcg aaaaagacta ctaaagggta tacaagatca tgcccttgat    240
ctggtgccac gcggtagtcc cgggtatcca gggcccagag ggaacaagg accaacaggt    300 ccaaccggac ctgctggtcc acgaggtcta caaggtctac aaggtctaca aggtgaaaga    360
ggggaacaag gaccaacagg tcccgctggt ccacgaggtc tacaaggtga agagggggaa    420
caaggaccaa caggtctcgc tggtaaagcc ggtgaagctg gagccaaagg cgaaaccggc    480
cccgctggtc cacagggtcc acgtggtgaa caaggcccgc aaggtcttcc aggtaaagat    540

```
ggtgaagctg gtgctcaagg cccagcaggt ccaatgggtc ctgctggtga gcgaggtgaa    600
aaaggagaac ctggtaccca aggcgctaaa ggtgatcgcg gtgaaaccgg tccagtaggt    660
ccacgtggtg agcgaggcga agccggtccc gctggaaaag atggtgaacg tggtccagta    720
ggtccagctg gtaaggacgg ccaaaacggc aagatggtc ttccaggtaa agacggtaag    780
gacggccaaa acggtaaaga tggtcttcca ggtaagacg gtaaggacgg ccaaaacggt    840
aaagatggtc ttccaggtaa agacggtaag gacggtcaag atggtaaaga cggcctccca    900
ggtaaagacg gtaaagatgg cctcccaggt aaggacggta aggacggtca accaggtaaa    960
ccgggtaaat attaa                                                     975
```

<210> SEQ ID NO 14
<211> LENGTH: 324
<212> TYPE: PRT
<213> ORGANISM: Artificial Sequence
<220> FEATURE:
<223> OTHER INFORMATION: chemically synthesized bacterial collagen
      sequence

<400> SEQUENCE: 14

```
Met His His His His His His Asp Glu Gln Glu Glu Lys Ala Lys Val
1               5                   10                  15

Arg Thr Glu Leu Ile Gln Glu Leu Ala Gln Gly Leu Gly Gly Phe Glu
            20                  25                  30

Lys Lys Asn Phe Pro Thr Leu Gly Asp Glu Asp Leu Asp His Thr Tyr
        35                  40                  45

Met Thr Lys Leu Leu Thr Tyr Leu Gln Glu Arg Glu Gln Ala Glu Asn
    50                  55                  60

Ser Trp Arg Lys Arg Leu Leu Lys Gly Ile Gln Asp His Ala Leu Asp
65                  70                  75                  80

Leu Val Pro Arg Gly Ser Pro Gly Tyr Pro Gly Pro Arg Gly Glu Gln
                85                  90                  95

Gly Pro Thr Gly Pro Thr Gly Pro Ala Gly Pro Arg Gly Leu Gln Gly
            100                 105                 110

Leu Gln Gly Leu Gln Gly Glu Arg Gly Glu Gln Gly Pro Thr Gly Pro
        115                 120                 125

Ala Gly Pro Arg Gly Leu Gln Gly Glu Arg Gly Glu Gln Gly Pro Thr
    130                 135                 140

Gly Leu Ala Gly Lys Ala Gly Glu Ala Gly Ala Lys Gly Glu Thr Gly
145                 150                 155                 160

Pro Ala Gly Pro Gln Gly Pro Arg Gly Glu Gln Gly Pro Gln Gly Leu
                165                 170                 175

Pro Gly Lys Asp Gly Glu Ala Gly Ala Gln Gly Pro Ala Gly Pro Met
            180                 185                 190

Gly Pro Ala Gly Glu Arg Gly Glu Lys Gly Glu Pro Gly Thr Gln Gly
        195                 200                 205

Ala Lys Gly Asp Arg Gly Glu Thr Gly Pro Val Gly Pro Arg Gly Glu
    210                 215                 220

Arg Gly Glu Ala Gly Pro Ala Gly Lys Asp Gly Glu Arg Gly Pro Val
225                 230                 235                 240

Gly Pro Ala Gly Lys Asp Gly Gln Asn Gly Gln Asp Gly Leu Pro Gly
                245                 250                 255

Lys Asp Gly Lys Asp Gly Gln Asn Gly Lys Asp Gly Leu Pro Gly Lys
            260                 265                 270
```

```
Asp Gly Lys Asp Gly Gln Asn Gly Lys Asp Gly Leu Pro Gly Lys Asp
            275                 280                 285

Gly Lys Asp Gly Gln Asp Gly Lys Asp Gly Leu Pro Gly Lys Asp Gly
        290                 295                 300

Lys Asp Gly Leu Pro Gly Lys Asp Gly Lys Asp Gly Gln Pro Gly Lys
305                 310                 315                 320

Pro Gly Lys Tyr

<210> SEQ ID NO 15
<211> LENGTH: 12
<212> TYPE: PRT
<213> ORGANISM: Homo sapiens

<400> SEQUENCE: 15

Gly Glu Arg Gly Phe Pro Gly Glu Arg Gly Val Glu
1               5                   10

<210> SEQ ID NO 16
<211> LENGTH: 1026
<212> TYPE: DNA
<213> ORGANISM: Artificial Sequence
<220> FEATURE:
<223> OTHER INFORMATION: chemically synthesized bacterial collagen
      sequence

<400> SEQUENCE: 16
```

| | | | | |
|---|---|---|---|---|
| atgggaccac | cggcccggc | gggcccggcg | ggcccgcagg | gcccggcggg  cccggcgggc | 60 |
| gcgcagggcc | cggcgggccc | ggcgggcccg | cagggcccgg | cgggcccgca  gggcagcgcg | 120 |
| ggcgcgcagg | gcccgaaagg | cgataccggc | gcggcgggcc | cggcgggcga  agcgggcccg | 180 |
| aaaggcgaaa | ccggcgcggc | gggcccgaaa | ggcgataccg | gcggcggcgggc  ccggcgggc | 240 |
| ccgaaaggcg | ataccggtga | acgtggttt | ccgggtgaga | ggggcgtcga  gggcgcggcg | 300 |
| ggcgcgaccg | gcccgaaagg | cgaaaaaggc | gaaaccggcg | cggcgggccc  gaaaggcgat | 360 |
| aaaggcgaaa | ccggcgcggc | gggcccgaaa | ggcgataaag | gcgaaaccgg  cgcggcgggc | 420 |
| ccgaaaggcg | aaaaaggcga | aaccggcgcg | gtgggcccga | aaggcgataa  aggcgaaacc | 480 |
| ggcgcggcgg | gcccgaaagg | cgatcgcggc | gaaaccggcg | cggtgggccc  gaaaggcgat | 540 |
| aaaggcgaaa | ccggcgcggt | gggcccgaaa | ggcgataaag | gcgaaaccgg  cgcgattggc | 600 |
| ccgaaaggcg | ataaaggcga | taaaggcgat | aaaggcgatg | cgggcgtggc  gggcccgcag | 660 |
| ggcattcagg | gcgtgaaagg | cgataccgga | tatcccggcc | cgaaaggcga  tgcgggcccg | 720 |
| cagggcgcgc | cgggcacccc | gggcggcccg | agcattgaac | aggtgatgcc  gtggctgcat | 780 |
| ctgatttttg | atgcgtatga | agattataaa | gcgcagcgcg | cgcgcgaagc  gcgcgaactg | 840 |
| gaagaacgcc | tggcggcgga | agcgctggaa | caggcggcgc | gcgaagcggc  ggaacgcgaa | 900 |
| gtggcggcgg | cgattgaagc | ggcgaacgcg | gaagcggaaa | ttatgctgga  tgatgaaacc | 960 |
| catgcggaag | cggcaaaaa | aaaaaaaaaa | cgcaaacata | aagatcacca  ccatcaccat | 1020 |
| cattaa | | | | | 1026 |

```
<210> SEQ ID NO 17
<211> LENGTH: 341
<212> TYPE: PRT
<213> ORGANISM: Artificial Sequence
<220> FEATURE:
<223> OTHER INFORMATION: chemically synthesized bacterial collagen
      sequence
```

<400> SEQUENCE: 17

Met Gly Pro Pro Gly Pro Ala Gly Pro Ala Gly Pro Gln Gly Pro Ala
1               5                   10                  15

Gly Pro Ala Gly Ala Gln Gly Pro Ala Gly Pro Ala Gly Pro Gln Gly
            20                  25                  30

Pro Ala Gly Pro Gln Gly Ser Ala Gly Ala Gln Gly Pro Lys Gly Asp
        35                  40                  45

Thr Gly Ala Ala Gly Pro Ala Gly Glu Ala Gly Pro Lys Gly Glu Thr
    50                  55                  60

Gly Ala Ala Gly Pro Lys Gly Asp Thr Gly Ala Ala Gly Pro Ala Gly
65                  70                  75                  80

Pro Lys Gly Asp Thr Gly Glu Arg Gly Phe Pro Gly Glu Arg Gly Val
            85                  90                  95

Glu Gly Ala Ala Gly Ala Thr Gly Pro Lys Gly Glu Lys Gly Glu Thr
            100                 105                 110

Gly Ala Ala Gly Pro Lys Gly Asp Lys Gly Glu Thr Gly Ala Ala Gly
            115                 120                 125

Pro Lys Gly Asp Lys Gly Glu Thr Gly Ala Ala Gly Pro Lys Gly Glu
        130                 135                 140

Lys Gly Glu Thr Gly Ala Val Gly Pro Lys Gly Asp Lys Gly Glu Thr
145                 150                 155                 160

Gly Ala Ala Gly Pro Lys Gly Asp Arg Gly Glu Thr Gly Ala Val Gly
                165                 170                 175

Pro Lys Gly Asp Lys Gly Glu Thr Gly Ala Val Gly Pro Lys Gly Asp
            180                 185                 190

Lys Gly Glu Thr Gly Ala Ile Gly Pro Lys Gly Asp Lys Gly Asp Lys
        195                 200                 205

Gly Asp Lys Gly Asp Ala Gly Val Ala Gly Pro Gln Gly Ile Gln Gly
    210                 215                 220

Val Lys Gly Asp Thr Gly Tyr Pro Gly Pro Lys Gly Asp Ala Gly Pro
225                 230                 235                 240

Gln Gly Ala Pro Gly Thr Pro Gly Gly Pro Ser Ile Glu Gln Val Met
                245                 250                 255

Pro Trp Leu His Leu Ile Phe Asp Ala Tyr Glu Asp Tyr Lys Ala Gln
            260                 265                 270

Arg Ala Arg Glu Ala Arg Glu Leu Glu Arg Leu Ala Ala Glu Ala
        275                 280                 285

Leu Glu Gln Ala Ala Arg Glu Ala Ala Glu Arg Glu Val Ala Ala Ala
    290                 295                 300

Ile Glu Ala Ala Asn Ala Glu Ala Glu Ile Met Leu Asp Asp Glu Thr
305                 310                 315                 320

His Ala Glu Gly Gly Lys Lys Lys Lys Arg Lys His Lys Asp His
                325                 330                 335

His His His His
        340

<210> SEQ ID NO 18
<211> LENGTH: 1026
<212> TYPE: DNA
<213> ORGANISM: Artificial Sequence
<220> FEATURE:
<223> OTHER INFORMATION: chemically synthesized bacterial collagen
      sequence

<400> SEQUENCE: 18

```
atgggaccac ccggcccggc gggcccggcg ggcccgcagg gcccggcggg cccggcgggc      60
gcgcagggcc cggcgggccc ggcgggcccg cagggcccgg cgggcccgca gggcagcgcg     120
ggcgcgcagg gcccgaaagg cgataccggc gcggcgggcc cggcgggcga agcgggcccg     180
aaaggcgaaa ccggcgcggc gggcccgaaa ggcgataccg gcgcggcggg cccggcgggc     240
ccgaaaggcg ataccggtga acgtggtttc ccgggtgaga ggggcgtcga gggcgcggcg     300
ggcgcgaccg gcccgaaagg cgaaaaaggc gaaaccggcg cggcgggccc gaaaggcgat     360
aaaggcgaaa ccggcgcggc gggcccgaaa ggcgataaag gcgaaaccgg cgcggcgggc     420
ccgaaaggcg aaaaaggcga accggcgcg gtgggcccga aaggcgataa aggcgaaacc     480
ggcgcggcgg gcccgaaagg cgatcgcggc gaaaccggcg cggtgggccc gaaaggcgat     540
aaaggcgaaa ccggcgcggt gggcccgaaa ggcgataaag gcgaaaccgg cgcgattggc     600
ccgaaaggcg ataaaggcga taaaggcgat aaaggcgatg cgggatgtcc cggcccgcag     660
ggcattcagg gcgtgaaagg cgataccggc ctgcagggcc cgaaaggcga tgcgggcccg     720
cagggcgcgc cggcaccccc gggcggcccg agcattgaac aggtgatgcc gtggctgcat     780
ctgatttttg atgcgtatga agattataaa gcgcagcgcg cgcgcgaagc gcgcgaactg     840
gaagaacgcc tggcggcgga agcgctggaa caggcggcgc gcgaagcggc ggaacgcgaa     900
gtggcggcgc gattgaagc ggcgaacgcg aagcggaaa ttatgctgga tgatgaaacc      960
catgcggaag gcggcaaaaa aaaaaaaaaa cgcaaacata agatcacca ccatcaccat    1020
cattaa                                                              1026
```

<210> SEQ ID NO 19
<211> LENGTH: 341
<212> TYPE: PRT
<213> ORGANISM: Artificial Sequence
<220> FEATURE:
<223> OTHER INFORMATION: chemically synthesized bacterial collagen sequence

<400> SEQUENCE: 19

```
Met Gly Pro Pro Gly Pro Ala Gly Pro Ala Gly Pro Gln Gly Pro Ala
1               5                   10                  15

Gly Pro Ala Gly Ala Gln Gly Pro Ala Gly Pro Ala Gly Pro Gln Gly
            20                  25                  30

Pro Ala Gly Pro Gln Gly Ser Ala Gly Ala Gln Gly Pro Lys Gly Asp
        35                  40                  45

Thr Gly Ala Ala Gly Pro Ala Gly Glu Ala Gly Pro Lys Gly Glu Thr
    50                  55                  60

Gly Ala Ala Gly Pro Lys Gly Asp Thr Gly Ala Ala Gly Pro Ala Gly
65                  70                  75                  80

Pro Lys Gly Asp Thr Gly Glu Arg Gly Phe Pro Gly Glu Arg Gly Val
                85                  90                  95

Glu Gly Ala Ala Gly Ala Thr Gly Pro Lys Gly Glu Lys Gly Glu Thr
            100                 105                 110

Gly Ala Ala Gly Pro Lys Gly Asp Lys Gly Glu Thr Gly Ala Ala Gly
        115                 120                 125

Pro Lys Gly Asp Lys Gly Glu Thr Gly Ala Ala Gly Pro Lys Gly Glu
    130                 135                 140

Lys Gly Glu Thr Gly Ala Val Gly Pro Lys Gly Asp Lys Gly Glu Thr
145                 150                 155                 160
```

Gly Ala Ala Gly Pro Lys Gly Asp Arg Gly Glu Thr Gly Ala Val Gly
                165                 170                 175

Pro Lys Gly Asp Lys Gly Glu Thr Gly Ala Val Gly Pro Lys Gly Asp
            180                 185                 190

Lys Gly Glu Thr Gly Ala Ile Gly Pro Lys Gly Asp Lys Gly Asp Lys
        195                 200                 205

Gly Asp Lys Gly Asp Ala Gly Cys Pro Gly Pro Gln Gly Ile Gln Gly
    210                 215                 220

Val Lys Gly Asp Thr Gly Leu Gln Gly Pro Lys Gly Asp Ala Gly Pro
225                 230                 235                 240

Gln Gly Ala Pro Gly Thr Pro Gly Gly Pro Ser Ile Glu Gln Val Met
                245                 250                 255

Pro Trp Leu His Leu Ile Phe Asp Ala Tyr Glu Asp Tyr Lys Ala Gln
            260                 265                 270

Arg Ala Arg Glu Ala Arg Glu Leu Glu Glu Arg Leu Ala Ala Glu Ala
        275                 280                 285

Leu Glu Gln Ala Ala Arg Glu Ala Ala Glu Arg Glu Val Ala Ala Ala
    290                 295                 300

Ile Glu Ala Ala Asn Ala Glu Ala Glu Ile Met Leu Asp Asp Glu Thr
305                 310                 315                 320

His Ala Glu Gly Gly Lys Lys Lys Lys Arg Lys His Lys Asp His
                325                 330                 335

His His His His His
        340

<210> SEQ ID NO 20
<211> LENGTH: 1026
<212> TYPE: DNA
<213> ORGANISM: Artificial Sequence
<220> FEATURE:
<223> OTHER INFORMATION: chemically synthesized bacterial collagen
      sequence

<400> SEQUENCE: 20
atgggaccac ccggcccggc gggcccggcg ggcccgcagg gccggcgggc cccggcgggc      60
gcgcagggcc cggcgggccc ggcgggcccg cagggcccgg cgggcccgca gggcagcgcg     120
ggcgcgcagg gcccgaaagg cgataccggc gcggcgggcc cggcgggcga agcgggcccg     180
aaaggcgaaa ccggcgcggc gggcccgaaa ggcgataccg gcgcggcggg cccggcgggc     240
ccgaaaggcg ataccggtga acgtggtttc ccgggtgaga ggggcgtcga gggcgcggcg     300
ggcgcgaccg gcccgaaagg cgaaaaaggc gaaaccggcg cggcgggccc gaaaggcgat     360
aaaggcgaaa ccggcgcggc gggcccgaaa ggcgataaag gcgaaaccgg cgcggcgggc     420
ccgaaaggcg aaaaaggcga aaccggcgcg gtgggcccga aaggcgataa aggcgaaacc     480
ggcgcggcgg gcccgaaagg cgatcgcggc gaaaccggcg cggtgggccc gaaaggcgat     540
aaaggcgaaa ccggcgcggt gggcccgaaa ggcgataaag gcgaaaccgg cgcgattggc     600
ccgaaaggcg ataaaggcga taaaggcgat aaaggcgatg cgggatgtcc cggcccgcag     660
ggcattcagg gcgtgaaagg cgataccgga tatcccggcc cgaaaggcga tgcgggcccg     720
cagggcgcgc cgggcacccc gggcggcccg agcattgaac aggtgatgcc gtggctgcat     780 ctgattttg atgcgtatga agattataaa gcgcagcgcg cgcgcgaagc gcgcgaactg     840
gaagaacgcc tggcggcgga agcgctggaa caggcggcgc gcgaagcggc ggaacgcgaa     900
gtggcggcgg cgattgaagc ggcgaacgcg gaagcggaaa ttatgctgga tgatgaaacc     960

-continued

```
catgcggaag gcggcaaaaa aaaaaaaaaa cgcaaacata agatcacca ccatcaccat   1020 cattaa                                                              1026
```

<210> SEQ ID NO 21
<211> LENGTH: 341
<212> TYPE: PRT
<213> ORGANISM: Artificial Sequence
<220> FEATURE:
<223> OTHER INFORMATION: chemically synthesized bacterial collagen sequence

<400> SEQUENCE: 21

```
Met Gly Pro Pro Gly Pro Ala Gly Pro Ala Gly Gln Gly Pro Ala
1               5                   10                  15

Gly Pro Ala Gly Ala Gln Gly Pro Ala Gly Pro Ala Gly Pro Gln Gly
            20                  25                  30

Pro Ala Gly Pro Gln Gly Ser Ala Gly Ala Gln Gly Pro Lys Gly Asp
            35                  40                  45

Thr Gly Ala Ala Gly Pro Ala Gly Glu Ala Gly Pro Lys Gly Glu Thr
        50                  55                  60

Gly Ala Ala Gly Pro Lys Gly Asp Thr Gly Ala Ala Gly Pro Ala Gly
65              70                  75                  80

Pro Lys Gly Asp Thr Gly Glu Arg Gly Phe Pro Gly Glu Arg Gly Val
            85                  90                  95

Glu Gly Ala Ala Gly Ala Thr Gly Pro Lys Gly Glu Lys Gly Glu Thr
            100                 105                 110

Gly Ala Ala Gly Pro Lys Gly Asp Lys Gly Glu Thr Gly Ala Ala Gly
            115                 120                 125

Pro Lys Gly Asp Lys Gly Glu Thr Gly Ala Ala Gly Pro Lys Gly Glu
            130                 135                 140

Lys Gly Glu Thr Gly Ala Val Gly Pro Lys Gly Asp Lys Gly Glu Thr
145             150                 155                 160

Gly Ala Ala Gly Pro Lys Gly Asp Arg Gly Glu Thr Gly Ala Val Gly
            165                 170                 175

Pro Lys Gly Asp Lys Gly Glu Thr Gly Ala Val Gly Pro Lys Gly Asp
            180                 185                 190

Lys Gly Glu Thr Gly Ala Ile Gly Pro Lys Gly Asp Lys Gly Asp Lys
            195                 200                 205

Gly Asp Lys Gly Asp Ala Gly Cys Pro Gly Pro Gln Gly Ile Gln Gly
            210                 215                 220

Val Lys Gly Asp Thr Gly Tyr Pro Gly Pro Lys Gly Asp Ala Gly Pro
225             230                 235                 240

Gln Gly Ala Pro Gly Thr Pro Gly Gly Pro Ser Ile Glu Gln Val Met
            245                 250                 255

Pro Trp Leu His Leu Ile Phe Asp Ala Tyr Glu Asp Tyr Lys Ala Gln
            260                 265                 270

Arg Ala Arg Glu Ala Arg Glu Leu Glu Glu Arg Leu Ala Ala Glu Ala
            275                 280                 285

Leu Glu Gln Ala Ala Arg Glu Ala Ala Glu Arg Glu Val Ala Ala Ala
            290                 295                 300

Ile Glu Ala Ala Asn Ala Glu Ala Glu Ile Met Leu Asp Asp Glu Thr
305             310                 315                 320
```

```
His Ala Glu Gly Gly Lys Lys Lys Lys Arg Lys His Lys Asp His
            325                 330                 335
His His His His His
            340

<210> SEQ ID NO 22
<211> LENGTH: 12
<212> TYPE: PRT
<213> ORGANISM: Artificial Sequence
<220> FEATURE:
<223> OTHER INFORMATION: integrin binding sequence

<400> SEQUENCE: 22

Gly Glu Arg Gly Phe Pro Gly Glu Arg Gly Val Glu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: heparin binding sequence

<400> SEQUENCE: 23

Gly Arg Pro Gly Lys Arg Gly Lys Gln Gly Gln Lys
1               5                   10

<210> SEQ ID NO 24
<211> LENGTH: 4
<212> TYPE: PRT
<213> ORGANISM: Artificial Sequence
<220> FEATURE:
<223> OTHER INFORMATION: chemical reactant
<220> FEATURE:
<221> NAME/KEY: MISC_FEATURE
<222> LOCATION: (1)..(1)
<223> OTHER INFORMATION: There is a bromoacetyl attached to the Gly

<400> SEQUENCE: 24

Gly Arg Arg Arg
1

<210> SEQ ID NO 25
<211> LENGTH: 5
<212> TYPE: PRT
<213> ORGANISM: Artificial Sequence
<220> FEATURE:
<223> OTHER INFORMATION: chemical reactant
<220> FEATURE:
<221> NAME/KEY: MISC_FEATURE
<222> LOCATION: (1)..(1)
<223> OTHER INFORMATION: There is a bromoacetyl attached to the Gly

<400> SEQUENCE: 25

Gly Arg Gly Asp Ser
1               5

<210> SEQ ID NO 26
<211> LENGTH: 4
<212> TYPE: PRT
<213> ORGANISM: Artificial Sequence
<220> FEATURE:
<223> OTHER INFORMATION: synthetic sequence

<400> SEQUENCE: 26

Tyr Arg Arg Arg
1
```

MODIFIED BACTERIAL COLLAGEN-LIKE PROTEINS

CROSS-REFERENCE TO OTHER APPLICATIONS

The present application claims priority from Australian provisional patent application no. 2013903444 entitled 'Modification of bacterial collagen-like proteins' filed 9 Sep. 2014, the entire contents of which are herein incorporated by reference.

All publications, patents, patent applications and other references cited herein are incorporated by reference in their entirety as if each individual publication, patent, patent application or other reference were specifically and individually indicated to be incorporated by reference.

FIELD OF THE DISCLOSURE

The present disclosure relates to recombinant or synthetic collagen-like proteins comprising at least one triple-helical domain and wherein the collagen-like protein is modified compared to a native bacterial collagen-like sequence.

BACKGROUND

Collagens are the major structural proteins in the extracellular matrix of animals and are defined by a characteristic triple-helix structural motif that requires a (Gly-Xaa-Yaa)$_n$ repeating sequence. The amino acids found in the Xaa and Yaa positions are frequently proline, where Pro in the Yaa position is post-translationally modified to hydroxyproline (Hyp) which enhances triple-helical stability. In humans, a family of at least 28 collagen types is present, each with type-specific biological and structural functions. The triple helical motif is also present in other proteins, such as macrophage scavenger receptors, collectins and C1q.

The most abundant collagens are the interstitial, fibril-forming collagens, particularly type I collagen. These collagens form the major tissue structures in animals through forming fibre bundle networks that are stabilized by specific cross-links to give stability and strength to the tissues. In contrast to the 'major' fibril forming collagens (types I, II and III) the 'minor' collagens are generally less broadly distributed and are typically found in particular tissue locations where the minor collagen may be a significant and critical component; e.g., type X collagen in hypertrophic cartilage or the type IV collagen in basement membranes.

The majority of commercial quantities of collagen have been derived from animals, such as bovine sources, but with the concern of transmissible diseases, especially bovine spongiform encephalopathy ('mad cow disease'). Moreover, animal-derived collagen is limited in that extracted collagens cannot be designed and modified to enhance or change specific biological or functional properties. Collagens are subject to extensive post-translational modifications both prior to and after deposition in the extracellular matrix. In particular, the fibrillar collagens are subjected to intra- and inter-molecular cross-linking that continues over the life of the molecule in the extracellular space. Thus, the amount of cross-linking present in collagens is influenced by, among other things, the age and physiology of the tissue from which the collagen is harvested. These differences influence both the extractability of collagens from tissue and the biophysical characteristics of these collagens. As a result, collagens isolated from tissues exhibit significant lot-to-lot variability and, as bulk materials, are often analytically intractable.

Accordingly, attention has shifted away from isolation of animal collagen towards production of recombinant collagens. Further, the use of recombinant DNA technology is desirable in that it allows for the potential production of synthetic collagens, collagen-like molecules and triple helical proteins which may include, for example, exogenous biologically active domains (i.e. to provide additional protein function) and other useful characteristics (e.g. improved biocompatibility and stability).

Host systems such as yeast have been explored to recombinantly produce human coded collagen. However, for production of human mimics, yeast systems are complicated by the need to introduce genes for proline-4 hydroxylase to form the Hyp residues needed for stability of mammalian collagens. Typically, recombinant mammalian coded collagens are expressed in *Pichia*, which requires oxygen addition to get maximum hydroxylation, as well as methanol addition for induction, adding complexity to the system.

Other collagen-like material which does not require post translational modification has been sought as replacement to hydroxylated human collagen. Recently, research on bacterial genomes has indicated there are many putative bacterial proteins that contain Gly as every third residue and a high proline content, suggesting that collagen-like, triple-helical structures/domains may be present in certain bacterial derived proteins (Peng Y et al (2010) *Biomaterials* 31(10): 2755-2761; Yoshizumi A et al (2009) *Protein Sci* 18:1241-1251). Furthermore, several of these proteins have been shown to form triple-helices that are stable around 35-38° C., despite the absence of Hyp. The triple helical composition has been confirmed in a number of cases. Examples include cell surface proteins on certain bacterial cells and filaments on *Bacillus anthracis* spores. It has been postulated that expression of such collagen-like constructs in prophages present in pathogenic *E coli* strains appear to be responsible for dissemination of virulence-related genes through infection (Bella J et al (2012) 7(6) PLoS 1 e37872). Furthermore, the knowledge on how amino acid sequence contributes to the structure and stability of a triple-helix motif also allows for the design of novel triple-helical collagen-like molecules that will be stable without the need for post-translational modifications.

Collagen has been used in many applications, including as a biomedical material where it has been shown to be safe and effective in a variety of medical products in various clinical applications (Ramshaw et al, J Materials Science, Materials in Medicine, (2009), 20(1) pg S3-S8). The bacterial collagen-like proteins also have appropriate characteristics for biomedical applications, including a lack of immunogenicity and no cytotoxicity.

Non-animal sources of collagen or synthetic triple helical proteins when recombinantly produced may lack the desired interactions that stabilise protein aggregates and which are normally present in native animal collagens. In part, this is because such proteins lack hydroxyproline which is a stabilising feature found within most animal collagens, and they also lack the specialised mammalian crosslinking sites. For certain applications, bacterially derived collagen-like proteins may not have the desired functionality for proposed medical or non-medical use applications, for example as a biomedical product. By way of illustration, the Scl2 collagen-like gene from *S. pyogenes* behaves like a "blank slate" as it shows few, if any interactions with mammalian cells. It would be advantageous if such molecules could be modified to enable their functionality to also be modified.

The ability to produce collagen-like or triple helical proteins from non-animal sources which exhibit enhanced stability would be highly desirable for all applications in which animal-derived collagen would normally be used. Furthermore, modifications which improve the stability of a recombinant collagen-like or triple-helical protein could also be exploited to further introduce a required functionality.

Accordingly, there is a need for a method that allows for specific, controlled modification of recombinantly or synthetically produced non-mammalian collagen-like or triple-helical proteins, wherein such a method allows the introduction of various functional modifications to the protein.

SUMMARY OF THE DISCLOSURE

The present disclosure provides modified bacterial collagen-like proteins which can be readily produced by recombinant or synthetic means. In particular, the present disclosure relates to collagen-like proteins comprising at least one triple-helical domain (or collagen-like domain) which is modified compared to a native bacterial triple-helical domain sequence through the incorporation of one or more reactive amino acids within and/or adjacent to a triple-helical domain of the collagen-like protein. A nucleic acid sequence encoding the collagen-like proteins of the present disclosure can be synthesised and expressed in a non-animal host cell, including bacterial, yeast or plant host cells. Advantageously, compared to prior art methods the collagen-like proteins can be produced in various new, functional forms, with the function(s) at specific defined site(s). These include, for example, those enabling cross-linked forms for a variety of medical and non-medical applications. Furthermore, the collagen-like proteins can be produced utilising a method that does not result in denaturation, degradation or hydrolysis of the triple-helical domain of the collagen-like protein and thus the protein remains thermally stable during recombinant production.

In one embodiment, the present disclosure provides a collagen-like protein comprising one or more bacterial triple-helical domains having a GlyXaaYaa repeating motif, wherein at least one triple-helical domain is modified compared to a native bacterial triple-helical domain by the addition and/or substitution of one or more reactive amino acid residues located at one or more positions selected from:
(i) within said at least one triple-helical domain;
(ii) at or adjacent to the N and/or C-terminus of said at least one triple-helical domain; or
(iii) both (i) and (ii);
wherein said amino acid additions and/or substitutions provide chemical reactive sites which are not present in the native bacterial triple-helical domain.

In one example, the collagen-like protein is a recombinant protein. In one example, the collagen-like protein is a synthetically produced protein. In a further example, the collagen-like protein is a purified protein.

By "reactive amino acid residues" it is meant an amino acid residue having a side chain that can be chemically reacted with an appropriate reagent. In one example, the chemical reaction of the reactive amino acid(s) facilitates the attachment of a moiety. In another example, the chemical reaction of the reactive amino acid(s) provide cross-linking of triple-helical domains.

In one example, the amino acid is selected from the group consisting of cysteine (Cys or C), Tyrosine (Tyr or Y), Tryptophan (Trp or W), or Histidine (His or H) or combinations thereof. In a particular example, the amino acid is Cys or Tyr or combinations thereof.

Amino acid modification(s) may occur within the collagen-like protein at other positions (e.g. the C and/or N-terminus of a triple-helical domain) which can be engineered into the nucleic acid sequence that encodes for the recombinant collagen-like protein. Preferably, the amino acid is one that typically does not occur, or occurs in low frequency in native bacterial collagen triple-helical domains. Preferably, the modification is designed to enable a site specific functionality to the collagen-like protein; for example such functionality may include the attachment of a moiety or to improve properties of the protein, such as stability or solubility.

Without wishing to be bound by theory, persons skilled in the art would appreciate that the incorporation of a Trp (W) residues in the collagen-like protein may be useful for spectrophotometric quantification of the protein, but is not readily utilised for subsequent chemical modification reactions. Cysteine (Cys) is advantageous because its sulfur atom is involved in the formation of a sulfhydryl group which can be exploited for its reactivity. Cysteine can be readily oxidised to form a dimer containing a disulphide bridge between two cysteine residues. The properties of cysteine can thus be exploited to add a functional group or to facilitate cross-linking of the recombinant collagen-like protein.

With respect to tyrosine, its phenol functionality can be exploited. Tyrosine can be readily reacted by several different photochemical methods which will be familiar to persons skilled in the art. For example, Tyr residues can be photo-oxidised leading to formation of dityrosine bonds that link one or more collagen-like proteins. Furthermore, the advantage of utilising Tyr and Cys residues is that separate chemical reactions of Tyr and Cys can be carried out without interference. For example, a chemical reaction could be carried out to modify the Cys residues, followed by a chemical reaction to modify the Tyr residues or vice versa.

Methods for chemically reacting side chains of amino acid residues will be familiar to person skilled in the art. For example, the bacterial collagen-like protein of the present disclosure may be oxidised by methods known in the art or as described herein, to induce formation of disulfide bonds between cysteine residues resulting in cross-linking of the protein. In another example, the bacterial collagen-like protein of the present disclosure may be treated with a chemical entity that includes a maleimidyl functional group (e.g. bis-maleimidyl PEG) that reacts specifically with Cys residues and causes cross-linking. In a further example, the reaction may be with a chemical entity that includes an iodo- or bromo-acetyl functional group (e.g. bromoacetyl-Arg-Arg-Arg) that reacts specifically with Cys residues. In another example, the reaction may be effected with vinyl sulphone (bis-vinylsulfone PEG).

In another example, the amino acid side chain is reacted with a chemical entity that includes a phenolic functional group, such as a tyrosine residue on a peptide, or such as an entity modified by Bolton-Hunter reagent or by addition of tyramine, that reacts specifically with Tyr residues in the collagen-like protein to from dityrosine bonds by photo-oxidation.

Modification of the triple-helical domain sequence relative to a native bacterial collagen/collagen-like domain sequence may comprise the addition and/or substitution of at least one amino acid residue at one or more defined position(s) within and/or adjacent to a collagen-like or triple-helical domain sequence compared to a corresponding sequence of a native bacterial triple-helical domain sequence. The corresponding native bacterial collagen-like sequence may be used as template sequence from which the amino acid modifications are introduced.

The term "one or more positions" as used herein refers to a site(s) within a triple-helical domain, or at, or adjacent to a triple-helical domain of the collagen-like protein in which an amino acid substitution and/or addition occurs such that the resulting triple-helical domain sequence differs from a corresponding triple-helical domain sequence of a native bacterial collagen-like protein. In one example, the position is at or near the N-terminus of the triple-helical domain sequence. In another example, it is at or near the C-terminus of the triple-helical domain sequence. In a still further example, one or more positions include both the N and C termini of the triple-helical domain sequence. Preferably, the one or more positions are the N and/or C-terminus of the triple-helical domain of the collagen-like protein. In such examples, consecutive amino acids of a defined length may be added. For example, between 1 and 24 consecutive amino acids of any type (i.e. including at least one reactive amino acid) may be added, or between 1 and 20, or between 1 and 15, or between 1 and 10, or between 1 and 6 or between 1 and 5, or between 1 and 3 consecutive amino acids may be added at either the N and/or C termini of the triple-helical domain sequence.

In another example, additional Gly-Xaa-Yaa triplets may be added at the N and/or C terminus of the triple-helical domain. In one example, either the Xaa or Yaa residue in the triplet contains a Cys or Tyr residue. In one particular example, the N and/or C-terminal residue of the at least one triple-helical domain is substituted with between 1 and 15, or between 1 and 10, or between 1 and 8, or between 1 and 5 GlyXaaYaa motifs and wherein either the Xaa or Yaa position of the motif(s) is a Cys or Tyr residue. In another particular example, between 1 and 15, or between 1 and 10, or between 1 and 8, or between 1 and 5 GlyXaaYaa motifs are added to the N and/or C-terminal residue of the at least one triple-helical domain and wherein either the Xaa or Yaa position of the motif(s) is a Cys or Tyr residue. In one example, the GlyXaaYaa repeating motif is maintained. In another example, the GlyXaaYaa repeating motif is not maintained.

The term "at to the N and/or C-terminus" is understood to refer to the N and/or C most terminal amino acid residue of a triple-helical domain. For example, by way of illustration an N-terminal Gly-Xaa-Yaa motif in the native sequence of a triple-helical domain may be modified by substituting either the Xaa or Yaa residue with a Cys or Tyr residue. Accordingly such a modification results in substitution of the N and/or C terminal residue.

The term "adjacent to the N and/or C-terminus" is understood to mean the addition of amino acids comprising at least one reactive amino acid and/or addition of one or more Gly-Xaa-Yaa motif to the terminal N and/or C residue of a triple-helical domain wherein the terminal residue in the native sequence is retained. Accordingly, such a modification results in addition to amino acids to the terminal N and/or C residue.

In another example, the position(s) are within the at least one triple-helical domain of the collagen-like protein. In this example, it is preferable that a Cys and/or Tyr residue is substituted for either the Xaa or Yaa position (but not both) in a Gly-Xaa-Yaa triplet of the repeating motif. The insertion of an amino acid residue at the Xaa or Yaa position means that the integrity of the three dimensional structure can be substantially maintained. In this example, the number of substituted Cys and/or Tyr residues within the triple-helical domain is less that the number of Asp, Glu or Lys residues (whichever is lower) within the triple-helical domain. In another example, the amino acid addition and/or substitution within the at least one triple-helical domain does not maintain the GlyXaaYaa repeating motif.

In one example, between 1 and 10 reactive amino acid residues are introduced into the Xaa or Yaa position in a GlyXaaYaa motif of the at least one triple-helical domain. In another example, the number of amino acid substitutions within a single domain is between 1 and 10, or between 1 and 7, or between 1 and 5, or between 1 and 3, or 2 or 1.

In another example, the position(s) include both the addition of amino acid residues at the N and/or C-terminus of the triple-helical domain sequence as well as one or more single residue amino acid substitutions within the one or more triple-helical domains of the collagen-like protein as described above. Thus, the present disclosure also provides a collagen-like protein comprising a combination of any one of, or all of the amino acid additions and/or substitutions described herein.

In another example, collagen-like protein further comprises the addition and/or substitution of reactive amino acid residues between triple-helical domains.

In yet a further example, the collagen-like protein of the present disclosure comprises one or more triple-helical domains which are joined by a spacer sequence. The spacer sequence may be a linear sequence or alternatively a sequence which is a triple-helical sequence. In one example, the spacer sequence comprises at least 50 amino acid residues, at least 40 residues, at least 30 residues, at least 20 residues, at least 10 residues, or at least 5 residues. In a further example, the spacer comprises a sequence which preserves the three dimensional structure of the collagen-like protein. In a further example, the spacer sequence is proteolytically stable.

In another example, the spacer corresponds to an insert region providing a desired functionality. Such inserts can be engineered in the recombinant collagen-like protein to improve the properties of the collagen-like protein or which otherwise serve as a natural binding domain or biological cleavage sequence. Examples of inserts suitable for use are disclosed in, for example, WO 2010/091251. Suitable examples of insert regions include a thrombin/trypsin-like cleavage site, a heparin binding site, an integrin binding sequence, or cell surface receptor binding site or a combination of one or more of any of these.

Advantageously, the addition and/or substitution of Cys and/or Tyr residues with cross-linking ability can be exploited to produce a collagen-like protein of desired solubility. For example, by increasing the extent of cross-linking, it is possible to generate hydrogels which have various uses in medical and non-medical applications, as well as cosmetic applications.

In one example, the triple-helical domain (or collagen-like domain) of the collagen-like protein is a homotrimer.

The collagen-like protein of the present disclosure is preferably stable at mammalian body temperatures (i.e. between 35-40° C.).

In other examples, chimeric collagen-like proteins can be formed comprising one or more triple-helical domains each having a different sequence and hence functionality. For example, the collagen-like protein may comprise two or more triple-helical domains (or collagen-like domains) of two or more different bacterial triple-helical proteins which are optionally separated by a spacer as described above or a linker, wherein the linker if present, maintains the Gly-Xaa-Yaa repeating motif.

In one example according to any embodiment, the substituted and/or added reactive amino acid residues are chemically reacted with an agent to provide a modified collagen-like protein with altered properties. For example, the chemical reaction induces cross-linking of the reactive amino acid residues and/or provides for the attachment of a moiety to the reactive amino acid residue(s). In one example, the moiety is selected from a peptide, carbohydrate, small molecule, drug, antibody, toxin, imaging agent, binding sequence and polyethylene glycol (PEG)-based compounds. In another example, different moieties may be attached to the reactive amino acid residues.

The present disclosure also encompasses multimers and higher order structures in which collagen-like proteins of the present disclosure are linked through their N and C termini and/or through cross-linking of the reactive side chains of the Cys and/or Tyr residues present in the protein to form two dimensional sheets or three-dimensional structures.

Methods for introducing amino acid modifications into a sequence will be familiar to person skilled in the art. For example, single amino acid residue modifications can be introduced by site directed mutagenesis of the nucleotide sequence encoding a native bacterial collagen-like domain according to methods known in the art. In another example, the collagen-like sequence of the present disclosure is synthesised to include nucleotide residues that encode Cys and/or Tyr residues or which encode for a peptide sequence at the N and/or C-terminus of the collagen-like protein.

In another example, the reactive amino acid residues are further modified to introduce other functionalities. In a further example, the reactive amino acid residues are modified by introduction of azide or alkyne functionalities.

In another embodiment, the present disclosure provides a method of producing a recombinant collagen-like protein comprising one or more bacterial triple-helical domains having a GlyXaaYaa repeating motif, wherein at least one triple-helical domain is modified compared to a native bacterial triple-helical domain, the method comprising:
(i) providing a nucleotide sequence derived from a triple-helical forming domain sequence of a native bacterial collagen, said sequence being modified to comprise the addition and/or substitution of nucleotides encoding one or more reactive amino acid residues located at one or more positions selected from:
  (i) within said at least one triple-helical domain;
  (ii) at or adjacent to the N and/or C-terminus of said at least one triple-helical domain; or
  (iii) both (i) and (ii);
(ii) introducing the nucleotide sequence according to (i) into an expression vector which is capable of expressing the nucleotide sequence;
(iii) expressing the nucleotide sequence in a bacterial, yeast or plant host cell;
(iv) isolating the protein product of the expressed nucleotide sequence; and
(v) chemically reacting the substituted and/or added reactive amino acids with an agent to provide a modified collagen-like protein with altered properties.

In one example, the chemical reaction induces cross-linking of the reactive amino acid residues. In one example, the chemical reaction provides for the attachment of a moiety to the reactive amino acid residue. In one example, the moiety is selected from a peptide, carbohydrate, small molecule, drug, antibody, toxin, imaging agent, binding sequence and polyethylene glycol (PEG)-based compounds. In another example, different moieties may be attached to the reactive amino acid residues.

In one example, between 1 and 10 reactive amino acid residues are introduced into the Xaa or Yaa position in a GlyXaaYaa motif of the at least one triple-helical domain. In another example, the N and/or C-terminal residue of the at least one triple-helical domain is substituted with between 1 and 24 consecutive reactive amino acid residues. In another example, between 1 and 24 consecutive reactive amino acid residues are added to the N and/or C-terminal residue of the at least one triple-helical domain. For example, between 1 and 24 consecutive amino acids of any type (i.e. including at least one reactive amino acid) may be added, or between 1 and 20, or between 1 and 15, or between 1 and 10, or between 1 and 6 or between 1 and 5, or between 1 and 3 consecutive amino acids may be added at either the N and/or C termini of the collagen-like or triple-helical domain sequence.

In another example, the N and/or C-terminal residue of the at least one triple-helical domain is substituted with between 1 and 15, or between 1 and 10, or between 1 and 8, or between 1 and 5 GlyXaaYaa motifs and wherein either the Xaa or Yaa position of the motif(s) is a Cys or Tyr residue. In another example, between 1 and 15, or between 1 and 10, or between 1 and 8, or between 1 and 5 GlyXaaYaa motifs are added to the N and/or C-terminal residue of the at least one triple-helical domain and wherein either the Xaa or Yaa position of the motif(s) is a Cys or Tyr residue.

The nucleotide sequence according to the method may be generated through site directed mutagenesis of a native bacterial triple-helical forming sequence or alternatively the triple-helical forming sequence may be chemically synthesised using known methods.

In an example the nucleotide sequence further comprises a bacterial V-domain or equivalent sequence (e.g. coil-coil domain) to facilitate intracellular folding and processing of the expressed protein. In a particular example, the bacterial V-domain or equivalent sequence is provided at the N and/or C-terminus of the nucleotide sequence.

In another example, the nucleotide sequence further comprises sequence encoding a His$_6$ tag. In another example, the nucleotide sequence further comprises FLAG.

In one example according to the method of the present disclosure, one more nucleotides encoding a peptide sequence or Gly-Xaa-Yaa motif is added to the N and/or C terminal of the triple-helical forming domain nucleotide sequence. In another example, one or more nucleotides encoding Cys and/or Tyr residues are substituted for native residues within a triple-helical domain forming sequence.

It will be appreciated by persons skilled in the art that any modification to a nucleic acid triple-helical forming domain sequence described above, will, on expression of that sequence, be reproduced in each of the three chains that form a triple-helical domain of the collagen-like protein.

In an example, the nucleotide sequence encoding the recombinant bacterial collagen-like protein of the present disclosure may be codon optimised for expression in a bacterial, yeast or plant host cell.

The expression vector may any expression vector which is capable of expressing a nucleotide sequence of the present disclosure in a bacterial, yeast or plant cell. While not limited thereto, the bacterial expression vector may be a cold shock vector and the recombinant triple-helical protein may be expressed in the microorganism (e.g. E. coli) at temperatures below 37° C. and in certain examples, at temperatures of about 15 to 23° C. In a further example, the expression vector may be a pET vector (Novagen).

In another example, the expression vector is a yeast expression vector selected from pHIL-D2, pPIC3.5, pHIL-SI, pPIC9, pPICZ, pA0815, pBLADE, pBLARG, YepFlag1, pAMH110 or pBLURA.

In another example, the expression vector is a plant expression vector. Examples of plant expression vectors are known in the art and may include, for example pBI121, pCAmbia2301, pEAQ-HT-DEST, or PVX expression vector.

The collagen-like protein encoded by the expression vector is preferably thermally stable at mammalian body temperature (i.e. between 35 and 40° C.) or can be made stable post purification by modification.

In a further example according to a method of the present disclosure, the expressed collagen-like protein is purified. Various methods known in the art and are discussed elsewhere in this disclosure. Purification of the expressed collagen-like protein may be achieved by various methods, including acid precipitation of contaminating proteins followed by proteolysis of any remaining contaminating proteins as described in AU2013900990, or by the use of a tag label, such as His$_6$ tag or a Flag tag which allow purification by specific affinity columns. Other methods are also applicable and are known to those skilled in the art. The protein may be collected, for example by precipitation by ammonium sulfate or by a polymer, or by ultrafiltration, or by batch absorption and elution, for example using an ion exchange resin.

In a preferred method, the collagen-like protein is purified according to the method described in co-pending application PCT/AU2014/000303.

It will be appreciated by persons skilled in the art that the host cell which is transformed or transfected with a sequence encoding the collagen-like protein of the present disclosure is cultured under conditions suitable to cause expression of the introduced sequence. In some examples, the collagen-like protein will be produced intracellularly in which case it will be necessary to extract it from the cell. Extraction may be achieved by mechanical or chemical (e.g. enzymatic) means known to persons skilled in the art. Examples, of mechanical extraction processes may include one or more of the following, sonication, microfluidisation, lysis in a French Press or similar apparatus, osmotic shock, and disruption by vigorous agitation/milling with glass, ceramic or steel beads. Alternatively, or in conjunction with a mechanical extraction, an enzymatic extraction can also be employed. Examples, of agents suitable for enzymatic extraction include lysozyme, lysostaphin, zymolase, cellulose, mutanolysin, glycanases, proteases, mannose etc.

In some examples, the collagen-like protein is secreted from the host cell (i.e. produced extracellularly as is the case in some yeast systems). Under those circumstances, extraction is not necessary. However, the cell culture extract may be concentrated thus creating an homogenate or filtrate by methods known in the art to obtain a solution comprising the recovered soluble collagen-like construct. In another example, the cell culture medium is concentrated with the collagen-like protein by cross-flow filtration.

Cellular contaminants and debris from the recombinant collagen-like protein containing cell culture extract or homogenate are removed.

The bacterial host cell may be selected from, but not limited to *Escherichia, Bacillus, Enterobacter, Azotobacter, Erwinia, Pseudomonas, Klebsiella, Proteus, Salmonella, Serratia, Shigella, Rhizobia, Vitreoscilla* and *Paracoccus*. In one example, the bacterial host is *Escherchia coli*. Suitable *E. coli* hosts include *E. coli* BL21 strain (Life Sciences), *E. coli* W3110 (ATCC 27,325), *E. coli* 294 (ATCC 31,446), and *E. coli* X1776 (ATCC 31,537).

The yeast host cell may be selected from *Pichia pastoris, Hansenula polymorpha, Saccharomyces cerevisiae, Kluyveromyces lactis, Schwanniomyces occidentis, Schizosaccharomyces pombe, Trichoderma reesei* and *Yarrowia lipolytica*.

The plant host cell may be selected from tobacco, maize, wheat, barley, as well as lower plants such as microalgae such as *Chlorella vulgaris*.

Organisms from which the bacterial collagen-like sequence can be derived include, but are not limited to:
  (i) one or more DNA sequences isolated from pathogenic or non-pathogenic bacterial organisms including. For example, the triple-helical sequence can include collagen-like domains derived from one or more of *S. pyogenes, Methylobacterium* sp4-46, *Solibacter usitatus, Streptococcus equi* SclC, *Bacillus anthracis, Bacillus cereus, Clostridium perfringens, Rhodopseudomonas palustris, Streptococcus pneumoniae* A;
  (ii) one or more DNA sequences isolated from organisms selected from, but not limited to *Corynebacterium diphtheria*, Actinobacteria (e.g., *Mycobacterium gilvum, Mycobacterium tuberculosis, Mycobacterium vanbaalenii, Nocardioides* species, *Rubrobacter xylanophilus, Salinispora arenicola, Salinispora tropica*, and *Streptomyces* species), Alphaproteobacteria (e.g., *Anaplasma* species, *Methylobacterium radiotolerans, Nitrobacter winogradskyi, Paracoccus denitrificans, Rhizobium leguminosarum, Rhodobacter sphaeroides, Rhodopseudomonas palustris, Sphingomonas wittichii*, and *Wolbachia* species), Bacteroidetes (e.g., *Bacteroides thetaiotaomicron*), Betaproteobacteria (e.g., *Azoarcus* species, *Burkholderia ambifaria, Burkholderia cenocepacia, Burkholderia phymatum, Burkholderia vietnamiensis, Dechloromonas aromatica, Polaromonas naphthalenivorans, Ralstonia eutropha, Ralstonia metallidurans, Ralstonia pickettii*, and *Rhodoferax ferrireducens*), Cyanobacteria (e.g., *Cyanothece* species, *Synechocystis* species, *Trichodesmium erythraeum*), Deinococcus (e.g., *Deinococcus radiodurans*), Deltaproteobacteria (e.g., *Anaeromyxobacter dehalogenans*), Epsilonproteobacteria (e.g., *Campylobacter curvus*), Firmicutes (e.g., *Bacillus clausii, Bacillus halodurans, Bacillus pumilus, Bacillus subtilis, Clostridium botulinum, Clostridium phytofermentans, Enterococcus faecalis, Geobacillus kaustophilus, Lactobacillus casei, Lactobacillus plantarum, Lactococcus lactis, Lysinibacillus sphaericus, Staphylococcus haemolyticus, Streptococcus agalactiae*, and *Streptococcus pneumoniae*), and Gammaproteobacteria (e.g., *Citrobacter koseri, Enterobacter* species, *Escherichia coli, Klebsiella pneumoniae, Legionella pneumophila, Photorhabdus luminescens, Pseudomonas aeruginosa, Pseudomonas entomophila, Pseudomonas putida, Psychrobacter cryohalolentis, Saccharophagus degradans, Salmonella enterica, Salmonella typhimurium, Serratia proteamaculans, Shewanella amazonensis, Shewanella baltica, Shewanella frigidimarina, Shewanella halifaxensis, Shewanella loihica, Shewanella oneidensis, Shewanella pealeana, Shewanella putrefaciens, Shewanella sediminis, Shewanella woodyi, Shigella boydii, Shigella dysenteriae, Shigella flexneri, Shigella sonnei*, and *Vibrio harveyi*).

Depending on the end use of the collagen-like protein, a polishing step of the expressed collagen-like protein may be employed to further concentrate and/or purify the recombinant protein once the host cell contaminants have been removed. Chromatography is one such technique that is commonly used to polish protein solutions. Examples of chromatographic processes that may be adopted include ion exchange chromatography, high performance liquid chromatography, electrophoresis, gel filtration chromatography, affinity chromatography and hydrophobic interaction chromatography. If the collagen-like protein has been precipitated by a neutral polymer, the precipitate will be low in salt and hence can be used directly for ion exchange chromatography if further purification is necessary.

For certain applications, the added and/or substituted Cys and/or Tyr residues in the collagen-like protein are modified. For example, the collagen-like protein may be subjected to a chemical reaction e.g. oxidation which results in linking Cys residues through the formation of double bonds resulting in crosslinking and thus enhanced stability of the protein. Alternatively or additionally, Cys residues may be chemically modified to provide attachment of a moiety.

Alternatively, the collagen-like protein may be cross-linked through Tyr residues and/or the Tyr residues chemically modified to provide attachment of a moiety.

In one example, a moiety is one which cannot be attached to the collagen-like protein by recombinant means.

A moiety according to the present disclosure may be selected from a peptide, carbohydrate, small molecule (e.g. metal binding ligands), drug, antibody, toxin, imaging agent, binding sequence and polyethylene glycol (PEG) compounds.

In another embodiment, the present disclosure provides a collagen-like protein produced by method of the present disclosure. In one example, the collagen-like protein comprises a combination of any one of, or all of the amino acid additions and/or substitutions as described herein.

In another embodiment, the present disclosure provides a biomaterial, cosmaceutical or therapeutic product comprising a collagen-like protein according to the present disclosure, or produced by a method according to the present disclosure.

In another embodiment, the present disclosure provides a method of treating a medical condition in a subject comprising administering a collagen-like protein according to the present disclosure, or produced by a method according to the present disclosure to a subject in need thereof.

In another embodiment, the present disclosure provides for the use of a collagen-like protein according to the present disclosure or produced by a method according to the present disclosure in medicine.

In another embodiment, the present disclosure provides an artificial collagen-based material for use in non-medical application(s) comprising a collagen-like protein according to the present disclosure, or produced by a method according to the present disclosure. In one example, the material is a sponge, film or hydrolysed collagen-like protein.

In another embodiment, the present disclosure provides for the use of a collagen-like protein according to the present disclosure, or produced by a method according to the present disclosure in artificial collagen-based materials.

DESCRIPTION OF THE FIGURES

FIG. 1G shows a two-dimensional representation of Cysteine and/or Tyrosine amino acid additions at both the N and C terminal of the collagen-like domain.

FIG. 2D shows a two-dimensional representation of both the addition of Cysteine residues to either the C or N terminal of the collagen-like domain in combination with amino acid substitutions within the collagen-like domain.

KEY TO SEQUENCE LISTING

Figure 1:
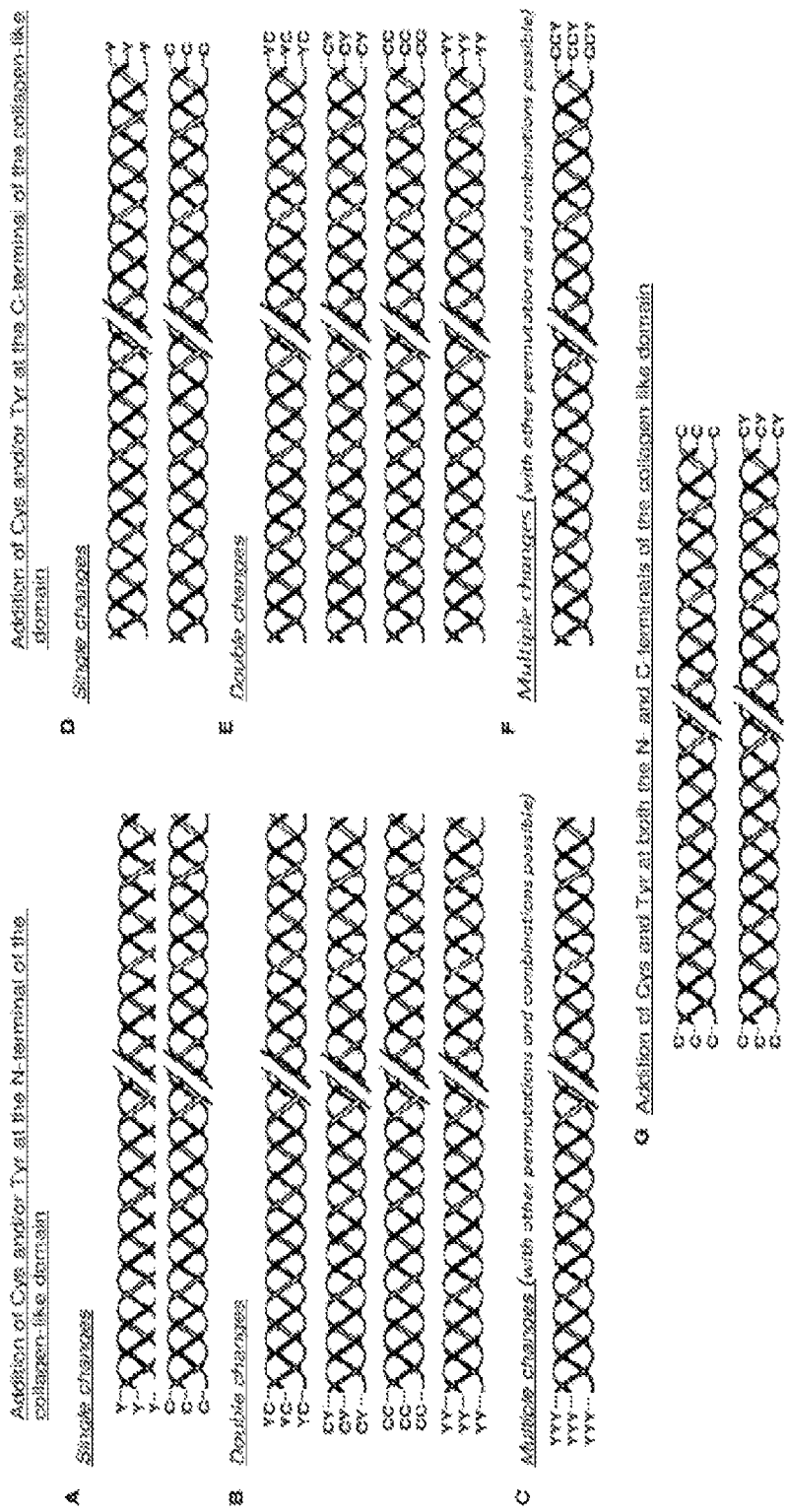
FIG. 1 shows a two-dimensional representation of Tyrosine (Y) or Cysteine (C) single, double, or multiple amino acid additions to either the N-terminal of the collagen-like domain (A (single), B (double), C (multiple)) or the C-terminal of the collagen-like domain (D (single), E (double), F (multiple)).
Figure 2:
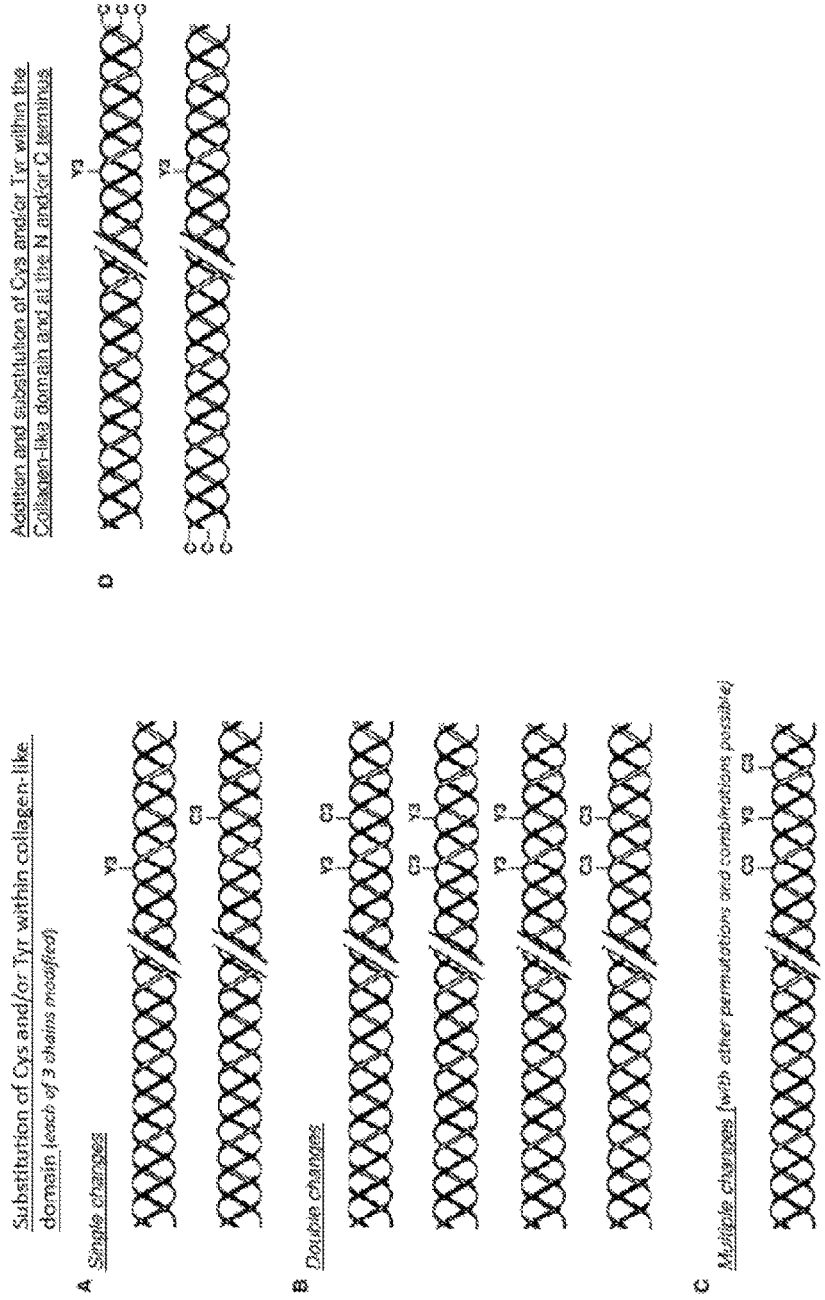
FIG. 2 shows a two-dimensional representation of single (A), double (B) or multiple (C) amino acid substitutions by Tyrosine (Y) or Cysteine (C) residues within the collagen-like domain.

SEQ ID NO: 1 is an amino acid sequence of thrombin/trypsin cleavage site;

SEQ ID NO: 2 is a nucleotide sequence of a bacterial collagen sequence with an introduced Tyr residue at the C-terminal;

SEQ ID NO: 3 is an amino acid sequence of a bacterial collagen sequence with an introduced Tyr residue at the C-terminal;

SEQ ID NO: 4 is a nucleotide sequence of a bacterial collagen sequence with an introduced Cys residue at the N-terminal;

SEQ ID NO: 5 is an amino acid sequence of a bacterial collagen sequence with an introduced Cys residue at the N-terminal;

SEQ ID NO: 6 is a nucleotide sequence of a bacterial collagen sequence with introduced Cys and Tyr residues both at the C terminal;

SEQ ID NO: 7 is an amino acid sequence of a bacterial collagen sequence with introduced Cys and Tyr residues both at the C terminal;

SEQ ID NO: 8 is an artificial sequence;

SEQ ID NO: 9 is a nucleotide sequence of a bacterial collagen sequence with introduced Tyr and Cys residues, all at the C-terminal;

SEQ ID NO: 10 is an amino acid sequence of a bacterial collagen sequence with introduced Tyr and Cys residues, all at the C-terminal;

SEQ ID NO: 11 is a nucleotide sequence of a bacterial collagen sequence with introduced Tyr and Cys residues, at both the N- (Cys) and C- (Tyr-Cys) terminals;

SEQ ID NO: 12 is an amino acid sequence of a bacterial collagen sequence with introduced Tyr and Cys residues, at both the N- (Cys) and C- (Tyr-Cys) terminals;

SEQ ID NO: 13 is the nucleotide sequence of a bacterial collagen sequence with introduced Tyr residues at the N- and C-terminals;

SEQ ID NO: 14 is the amino acid sequence of a bacterial collagen sequence with introduced Tyr residues at the N- and C-terminals;

SEQ ID NO: 15 is the amino acid integrin-binding sequence;

SEQ ID NO: 16 is a nucleotide sequence of a bacterial collagen sequence with an introduced Tyr residue within the triple-helical domain;

SEQ ID NO: 17 is an amino acid sequence of a bacterial collagen sequence with an introduced Tyr residue within the triple-helical domain;

SEQ ID NO: 18 is a nucleotide sequence of a bacterial collagen sequence with an introduced Cys residue within the triple-helical domain;

SEQ ID NO: 19 is an amino acid sequence of a bacterial collagen sequence with an introduced Cys residue within the triple-helical domain;

SEQ ID NO: 20 is a nucleotide sequence of a bacterial collagen sequence with introduced Tyr and Cys residues within the triple-helical domain;

SEQ ID NO: 21 is an amino acid sequence of a bacterial collagen sequence with introduced Tyr and Cys residues within the triple-helical domain.

GENERAL TECHNIQUES AND DEFINITIONS

Unless specifically defined otherwise, all technical and scientific terms used herein shall be taken to have the same meaning as commonly understood by one of ordinary skill in the art (e.g., in cell culture, molecular genetics, recombinant biology, immunology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present). Techniques for chemical coupling reactions are described for example in Hermanson GT (2008) Bioconjugate Techniques $2^{nd}$ Edition, Academic Press.

The term "and/or", e.g., "X and/or Y" shall be understood to mean either "X and Y" or "X or Y" and shall be taken to provide explicit support for both meanings or for either meaning. Furthermore, a list or features including the phrase "and/or" between the second last and last feature means that any one or more the listed features may be present in any combination.

Reference to the singular form is also understood to imply the inclusion of plural forms.

The term "plant" includes whole plants, vegetative structures (for example, leaves, stems, roots), floral organs/structures, seed (including embryo, endosperm, and seed coat), plant tissue (for example, vascular tissue, ground tissue, and the like), cells and progeny of the same.

The term "collagen-like protein" as used herein is understood as referring to a protein comprising at least one triple-helical domain. The term encompasses variants and fragment(s) of the collagen-like protein and functional equivalents and derivatives thereof which preferably retain at least one structural or functional characteristic of a collagen-like protein, (i.e. Gly Xaa Yaa)n sequence). The collagen-like protein may also include additional non-triple helical protein sequence which may be proteolytically stable and/or non-triple-helical inserts that may be either naturally or by design proteolytically stable depending upon the methodology used for removal of host cell proteins. A protein of the disclosure included within the term "collagen-like" includes a protein designed to comprise a sequence of Gly-Xaa-Yaa triplets as described above.

As used herein, the term "triple-helical domain" or "collagen-like (CL) domain" as used herein refers a homotrimeric protein derived from a native bacterial collagen-like sequence which comprises at least one region having the general peptide formula (Gly Xaa Yaa)$_n$, in which Gly is glycine, Xaa and Yaa represent the same or different amino acids (the identities of which may vary from Gly Xaa Yaa triplet to Gly Xaa Yaa triplet). The protein consists of three chains characterised by the repeating Gly Xaa Yaa repeating motif which are folded into a triple helical protein conformation. The triple-helical domain may be of any length, but preferably between 1-200 repeating Gly-Xaa-Yaa motifs. Typically, the native bacterial collagen-like (Cl) domain sequence contains a significantly higher proportion of threonine and glutamine in the Yaa position with a propensity for the Xaa position to be proline, alanine or serine. Further, a collagen-like domain will typically comprise a triple-helical three dimensional structure.

The term "triple-helical forming domain sequence" as herein refers to a nucleotide sequence which encodes an amino acid sequence composed of tandem repeats of a (Gly-Xaa-Yaa)n motif, wherein Xaa and Yaa are any other amino acid residues, that is capable of folding or associating with two other chains to form a triple helix or triple-helical domain.

The term "homotrimeric protein" refers to a collagen-like (CL) domain or triple-helical domain in which all three chains of the triple helix are the same.

The term "native bacterial collagen-like protein" as used herein refers to an isolated sequence that is substantially the same as a sequence derived from nature. A native sequence can have the same amino acid sequence of, e.g. naturally occurring bacterial collagen. The term "corresponding sequence" refers to the native bacterial collagen-like protein sequence which is used as a template for amino acid modification according to the present disclosure.

The term "culture" as used herein refers to the propagation of a host cell in a medium that leads to their growth and all the consequent subcultures.

The term "fragment" as used herein refers to a portion of the native amino acid or nucleotide sequence of a collagen-like protein or domain, and in particular the functional derivatives of the collagen-like protein.

The term "amino acid" as used herein refers to any chemical entity that is able to form or be present in a polypeptide sequence, and includes imino acids such as proline, and also other residues that can be introduced through adaptation of the intracellular protein synthesis pathways.

By "thermally stable" it is meant the extent to which the collagen-like protein (or triple-helical domain of a protein) maintains its triple-helical three dimensional structure at a given temperature. A degree of tolerance in the extent to which the triple-helical structure is destabilised is permitted according to the present disclosure, however, it is preferable that at least 70% of the collagen-like protein is maintained in the three-dimensional triple helical form. Persons skilled in the art will be aware of certain agents or additives that may be added during the processing of the collagen-like protein which assist in maintaining the thermal stability of the triple-helical collagen-like protein. For example, agents such as ethylene glycol or trimethylamine N-oxide (TMAO) may be added or other additives that provides stability such as for example, polyvinyl alcohol, polyvinylpyrrolidone, polyethylene glycol (PEG) or derivatives thereof, methylcellulose, agarose, dextrins, hydroxyethyl starches.

By "purified" it is meant that the collagen-like protein is separated from cellular components or other contaminating molecules or chemicals with which it is associated in the chemical synthesis or recombinant production thereof.

DETAILED DESCRIPTION OF THE DISCLOSURE

Gene Modification

The nucleotide sequence encoding the collagen-like protein of the present disclosure can be produced synthetically using methods known in the art. Typically, the "backbone" sequence of the nucleotide sequence will be based on or derived from the sequence of a native bacterial collagen (so-called "corresponding sequence"). The nucleotide sequence will include triple-helical forming sequences that in the three-dimensional structure form the triple-helical or collagen-like (CL) domain of the protein.

The nucleotide sequence can be synthesised such that nucleic acid residues encoding a desired amino acid residue, for example a Cys, Tyr, Trp or His residue or combinations thereof are incorporated into the sequence at one or more desired positions anywhere within the sequence, preferably, within or at a terminus of a collagen-like or triple-helical domain. Preferably, residues are introduced encoding amino acids that are not typically found in native bacterial collagen. Additionally any further desired sequence may be incorporated for example, sequence encoding an insert region or a spacer or sequence or sequence positioned at the N and/or C terminus of a triple-helical forming sequence. Specific residues can be introduced in the designed sequence to provide chemical functionality to the encoded protein. Where multiple contiguous codons are introduced, they are preferably introduced at a terminal end of a triple-helical forming sequence so as not to substantially disrupt the three dimensional triple helical structure of the expressed protein or otherwise separated through the presence or introduction of intervening sequences, including intervening sequences that maintain the Gly-Xaa-Yaa repeating motif of a triple-helical protein.

The introduced residues could be further modified to introduce other functionalities, for example either Azide or alkyne functionalities that would then be available for further modifications via 'click-chemistry' at ambient temperature, potentially using a Cu catalyst (R A Evans (2007) The Rise of Azide-Alkyne 1,3-Dipolar 'Click' Cycloaddition and its Application to Polymer Science and Surface Modification Australian Journal of Chemistry 60(6):384-395).

Alternatively, a nucleotide sequence may be synthesised and if necessary any substitutions introduced by site-directed mutagenesis according to standard methods known in the art.

Collagen-Like Protein of the Disclosure

The addition and/or substitution of reactive amino acid residues, in particular Cys and/or Tyr residues within the collagen-like protein as described herein, and more particularly, within or adjacent to a triple-helical domain of the collagen-like protein, are designed to impart functional properties to the collagen-like protein for various therapeutic and non-therapeutic applications. The side chains of Cys and/or Tyr residues can be modified through chemical reaction to provide reactive side groups for attachment of a moiety. Alternatively, the side chains of Cys and/or Tyr residues can be modified through chemical reaction to provide cross-linking. Furthermore, depending upon the number of Cys and/or Tyr residues that are introduced into the collagen-like protein, the extent of cross-linking can be controlled. Accordingly the collagen-like protein of the present disclosure can be produced in any form ranging from highly soluble forms to highly cross-linked forms such as hydrogels.

The collagen-like protein of the present disclosure is comprised of one or more bacterially derived collagen-like (CL) or triple-helical domains wherein each CL or triple-helical domain is optionally separated by a non-collagen-like insert region. The insert region may be adapted to mimic natural breaks in the triple helical structure that are found within many human collagens or may provide a desired biological functionality (e.g. cell matrix metallo protease cleavage site, etc). The insert region may occur between individual CL domains/triple-helical domains or within a CL/triple-helical domain of the recombinant collagen-like protein. To ensure proper folding of the triple helical domain of the recombinant collagen-like protein, post translationally, a globular folding domain (e.g. V-domain) is preferably inserted at the N- and/or C-terminus of the recombinant construct.

In one example, the sequences which are suitable for use in the generation of the collagen-like proteins of the present disclosure may be recombinantly derived from native triple-helical proteins found in pathogenic or non-pathogenic bacterial organisms. For example, a bacterial collagen-like protein from *Streptococcus pyogenes* (Scl1 or Scl2), has been shown to form a stable triple-helix structure without the need for post-translational modification to form hydroxyproline. In a further example, the genome sequences of Enterohaemorrhagic *E coli* O157:H7 strains show multiple open-reading frames with collagen-like sequences that are absent from the common laboratory strain K-12 (Ghosh N et al. (2012) PLoS one e37872).

Alternative sources of native bacterial collagen-like proteins which can be produced recombinantly can be found in *Methylobacterium* sp4-46, *Solibacter usitatus, Streptococcus equi* SclC, *Bacillus anthracis, Bacillus cereus, Clostridium perfringens, Rhodopseudomonas palustris Streptococcus pneumoniae* A. Accordingly, the present disclosure extends to the sequences or fragments thereof obtained from such sources.

In another example, the collagen-like protein is a recombinant protein comprising two CL domain/triple-helical domain sequences, either the same or different, linked consecutively without disruption of the Gly-Xaa-Yaa repeat.

In another example, the collagen-like protein is a recombinant protein comprising an insert sequence separating each CL domain/triple-helical domain wherein the insert sequence is a non-collagen peptide sequence of about 1 to 50 imino acids or amino acids. These sequences may provide some biological functionality that is useful for the resulting biomaterial, prior to the modification(s) described the present disclosure.

The desired biological functionality prior to the modification(s) described by the present disclosure of the collagen-like protein may be derived from sequences that facilitate binding to the targeted cell type or otherwise provides a natural cleavage site for degradation in the body. Binding sequences may include the integrin binding sequence from type I collagen (GERGFPGERGVE) (SEQ ID NO: 22) and/or one of the heparin binding sequences from the collagen tail of acetylcholine esterase (GRPGKRG-KQGQK) (SEQ ID NO: 23). Cleavage sequence may include, but is not limited to, one or more sequences within the family of matrix metalloproteinase (MMP)s domains e.g. MMP-I, MMP-2, MMP-8, MMP-13 and MMP-18 which cleave type I, II and III collagens, and MMP-2 and MMP-9 which cleave denatured collagens. Insert sequences may also include partial sequences of the abovementioned binding or cleavage sequences.

Additional sequences known to achieve such functionality are also contemplated by the present disclosure.

The use of recombinant techniques allows the introduction of specific stable triple-helical motif sequences that impart greater stability, such as changes in charge pairs, or sequences that influence the proteins denaturation temperature or pI which in turn influences how it can be used in medicine.

The functional domains can be inserted within a collagen-like domain/triple-helical domain or between successive collagen-like domains or triple-helical domains. Also, more than one functional domain can be added, which could include multiple repeats within a CL domain/triple-helical domain, or across several repeats of collagen-like or triple-helical domains where either the same or different functions could be included. Similarly, multiple functional repeats could be included between CL domain/triple-helical domain repeats, or more complex combinations could be achieved using inserts within and between sequences. Together, all these approaches allow for design and manipulation of the expressed collagen-like proteins to provide specific biological functions that could provide enhanced biomedical products.

In a further example, chimeric collagen-like proteins (comprising CL domains/triple-helical domains from different bacteria species) are also encompassed in the present disclosure.

Expression of the Triple-Helical Sequence

A nucleic acid triple helical forming domain sequence can be produced synthetically by methods known in the art. The sequence of a native bacterial collagen can be used as a template from which the recombinant sequence is engineered.

Methods of producing a recombinant collagen-like protein of the present disclosure include isolating and cloning a nucleotide sequence encoding the collagen-like protein into a single nucleic acid vector and expressing the sequence using standard methods that are generally known in the art, such as those described in Molecular Cloning (Sambrook and Russell (2001)). In one example, nucleotide sequence encoding a non-collagen linker or insert sequence is also inserted into the vector. In another example, additional nucleotide sequence which may or may not facilitate protein folding of the collagen-like domain/triple-helical domain upon expression may be provided at either or both the amino terminus or carboxy terminus end of the triple helical forming sequence. Methods of producing triple-helical proteins are known in the art and are described in, for example US 20120282817, EP1809751 and WO 2012/117406.

In one example, the expression vector may be a cold shock vector and the recombinant protein may be expressed in the microorganism (e.g. *E. coli*) at temperatures below 37° C. and in certain examples, at temperatures of about 15-23° C. The resulting expression product is then isolated, purified and processed to result in aggregate formation, which may be used as one or more of the biomaterials described herein.

The expression construct of the present disclosure may be cloned into an bacterial host using methods known in the art and as described in manuals such as Molecular Cloning (Sambrook and Russel (2001)). The host cells may be transformed using any transfection, transformation or other similar technique known in the art for inserting an expression cassette into a microorganism. In one example, post transformation, cells may be initially grown on suitable culture media at 37° C. until reaching A600 of about 0.8 to 1.2. Cultures may then be shifted to 15° C. to induce protein expression of the collagen-like protein and incubated overnight to produce the protein. It will be appreciated that the incubation time and temperatures may be varied as required.

Transformation, positive transformant selection and culturing methods in yeast are disclosed in, for example U.S. Pat. Nos. 4,837,148; 4,855,231; 4,882,279; 4,929,555; 5,122,465; 5,324,639; 5,593,859 and 6,472,171.

Host Cells

The host cells according to the present disclosure are any convenient non-animal cells, including cells of bacterial, yeast and plant origin. The host cells of the present invention may be naturally occurring organisms or mutated organisms capable of producing the collagen-like proteins. In one example, the host organism is an organism or progeny thereof which has been transformed using recombinant DNA techniques with a heterologous DNA sequence that codes for the production of the collagen-like protein. In one example, the host cell is *E. coli*.

Recovery of the Expressed Triple-Helical Protein

Post-expression, cultured cells may be harvested by techniques known in the art. In one example, the cells are harvested by centrifugation and resuspended in suitable media to yield a fermentation broth/solution or homogenate.

The exact method of recovery of the expressed recombinant collagen-like protein will depend on the host cell and expression construct. In microbial host cells, the collagen-like protein will be trapped within the cell wall of the host cells, even though it has been transported out of the cytoplasm. In this instance, the host cells are disrupted to recover the collagen-like protein. Alternatively, cell walls may be removed or weakened to release the protein located in the periplasm. Disruption can be accomplished by any means known in the art, including sonication, microfluidisation, lysis in a French Press or similar apparatus, disruption by vigorous agitation/milling with glass beads, lysis of osmotically fragile mutant yeast strains, or enzymatic treatment(s). Where the collagen-like protein is recovered by lysis or disruption of the recombinant host cell, the lysis or disruption is typically carried out in a buffer of sufficient ionic strength and appropriate pH to allow the collagen-like protein to remain in soluble form. Such mechanical and enzymatic disruption methods will produce subcellular fragments that can be removed by centrifugation or by filtration to obtain a homogenate.

If the collagen-like protein is produced extracellularly, that is, as soluble secreted protein, the cells still need to be removed from the cell supernatant. Clarification is generally accomplished by centrifugation, but can also be accomplished by sedimentation and/or filtration.

Purification of Triple-Helical Proteins

A broth/solution or homogenate containing the soluble recombinant collagen-like protein of the present disclosure can be purified by any of a number of methods known to those skilled in the art. For example, the collagen-like protein can be purified from the homogenate through use of an acid precipitation step followed by a proteolytic digestion step to remove host cell proteins that are amenable to protease digestion as described in PCT/AU2014/000303.

Alternatively, the recombinant collagen-like protein can be recovered and purified using a chromatographic approach, preferably using affinity chromatography methods. For example, if the recombinant protein has a suitable tag attached, such as a histidine or a FLAG tag, then use of a metal affinity column or an antibody-based column respectively can be used to achieve recovery and purification. The resulting eluted recombinant collagen-like protein can then be further processed, for example by ultrafiltration, precipitation or other chromatographic approaches.

As used herein, a "tag" sequence can include a polypeptide sequence that is used to localize the collagen-like protein to purify it from a cell extract, to immobilise it for use in binding assays or to otherwise study its biological properties and/or function. Examples include polyhistidine tag ($His_6$), histidine-tryptophan sequences, FLAG peptide fragment, hemagglutin (HA) tag sequence, a myc tag sequence, a glutathionine-S-transferase tag sequence, a maltose binding protein (MBP) tag sequence, a green fluorescent protein tag sequence, a myc-pyruvate kinase tag sequence, an influenza virus hemagglutinin tag sequence or other tag sequences known in the art.

Polishing

If the collagen-like protein is required for medical use, it is preferable that it is further purified by polishing purification steps to achieve purity levels greater than 90%. Any polishing purification is suitable according to the present disclosure including, for example gel filtration, hydrophobic, affinity or ion exchange chromatography.

Chemical Modification

Chemical modification of the collagen-like protein may precede a polishing step or occur after polishing of the protein. Modification of proteins will be familiar to persons skilled in the art. The type of modification will depend upon the side chain of individual amino acids.

In one example, Cys residues may be modified through oxidation leading to the formation of disulfide bonds that link one or more molecules. Various oxidation states of cysteine are known e.g. cysteinyl radical, cysteine sulfenic acid, cysteine sulfinic acid, cysteine sulfonic acid, cysteine S-sulfate, cystine, cystine S-monoxide and cystine S-dioxide. Disulfides impart essential and often resilient structural stability in many proteins. One method for forming disulfide at cysteine is air oxidation which can be used to form internal disulfides when refolding proteins, to cross-link collagen-like proteins and to conjugate small molecules. Since air oxidation requires long reaction times and limited control of product distribution (e.g. mixed disulfide vs dimer) alternative protocols have been developed. Formation of disulfides on a protein can be accomplished by disulfide exchange, provided there is a thermodynamic preference for the disulfide formation on the protein. A known example is the reaction of 5,5-dithiobis(2-nitrobenzoate) (DTNB or Ellman's Reagent) with cysteine. The most general method for disulfide formation is the use of activated reagents. Iodine has been used as an oxidant, activating cysteine for the formation of mixed disulfides. Sulfenyl halides have also been demonstrated as suitable reagents for mixed disulfide formation. The thiol group of a cysteine side chain is target for chemoselective modification owing to the ease with which it can be derivatised. Methanethiosulfonate reagents and related activated thiols have traditionally been used for modification of cysteine residues for functional purposes. Iodoacetamides can be used in cysteine glycosylation.

Cysteines can also be modified by direct alkylation with suitable electrophiles. The conjugate addition of cysteine to Michael acceptors can be used to selectively alkylate the cysteine side chain. Maleimides, vinyl sulfones and related α, β unsaturated systems are the most widely used Michael acceptors. Modification may be by reaction with a chemical entity that includes an iodo- or bromo-acetyl functional group that reacts specifically with Cys residues. Modification may also be achieved by the use of di-vinylsulfone PEG or maleimidyl PEG according to known methods to introduce PEG compounds. Without wishing to be bound by theory, it is thought that the addition of PEG may assist in enhancing the solubility of the collagen-like protein.

In another example, modification may be by reaction with a chemical entity that includes a phenolic functional group, such as a tyrosine residue on a peptide, or such as an entity modified by Bolton-Hunter reagent or by addition of tyramine, that reacts specifically with Tyr residues in the collagen-like protein during photo-oxidation.

The formation of crosslinks involving tyrosine or phenolic entities may be achieved by various methods known to those skilled in the art. For example, photo-crosslinking may be achieved by adding to a solution (in PBS) of protein that has been modified to include additional Tyr residues, 2 mM [Ru$^{II}$(bpy)$_3$]Cl$_2$ and 10 mM sodium persulfate in PBS followed by irradiation for 20 sec at a distance of 20 mm with a LED dental curing lamp (430-480 nm, peak wavelength 455 nm±10 nm, 1200 mW/cm$^2$ at source, 3M ESPE™ S10 LED curing Light). The irradiation can be repeated 2 or 3 times. Other methods are also available to form crosslinks between tyrosine resides or tyrosine and phenolic entities. These include, but are not limited to, a citrate modified photo-Fenton reaction using citrate:Fe:H2O2 in molar ratio of 5:1:20/10, respectively at pH 5, with illumination by UV light at 370 nm. Also the cross-linking can be enzyme catalysed, for example using 0.25 M sodium borate/boric acid buffer, pH 8.4, at 37° C., with addition of horseradish peroxidase and followed immediately with 10 mM hydrogen peroxide to initiate the reaction and incubation at 37° C. for at least 1 hour.

A combination of modifications at cysteine and tyrosine residues may be employed according to the present disclosure.

Modification of amino acid side chains are known in the art and are described for example in F. Javier Lopez-Jaramillo, Fernando Hernandez-Mateo and Francisco Santoyo-Gonzalez (2012). Vinyl Sulfone: A Multi-Purpose Function in Proteomics, Integrative Proteomics, Dr. Hon-Chiu Leung (Ed.), ISBN:978-953-51-0070-6, InTech, which is incorporated by reference.

Stabilisation

If the purified collagen-like proteins are to be used as biomedical materials, they must be able to be fabricated into appropriate formats. Collagen-like proteins of the present disclosure can be formed into sponges and sheets. To help achieve these formats the collagen-like protein can be stabilised prior to use in medical application to improve its long term stability and mechanical strength if so desired. In some cases stabilisation may be achieved through the sequence modifications that have been introduced according to the present disclosure. Thus collagen-like proteins could, for example, be crosslinked through formation of disulfide bonds between Cys residues on different molecules, or through cross-linking agent that link one Cys to another. Alternatively, for example, the collagen-like proteins may be crosslinked through formation of dityrosine bonds between Tyr residues on different molecules, In addition, or alternatively, a wide variety of suitable stabilisation strategies are possible. Glutaraldehyde is a suitable chemical reagent for cross linking and widely used to improve in vivo stability of collagen materials. Irradiation or dehydrothermal cross-linking are suitable physical stabilisation technique.

In other examples, proper folding of the recombinant bacterial collagen-like protein of the present disclosure may be assisted using globular or variable domains. Such globular domains may be expressed directly or indirectly to the N-terminus and/or the C-terminus of the collagen-like domain and can facilitate both post-translational folding and refolding following heat denaturation. One non-limiting example of an N-terminus domain is the entirety of or a portion of a variable domain of the Scl2 sequence found in *Streptococcus pyrogenes*. A non-limiting example of a C-terminus variable domain may be isolated from the organism *Rhodopseudomonas palustris*.

The present disclosure however is not limited to these examples, and may also include similar or otherwise homologous globular proteins, coiled-coil forming sequences or foldons found in the microorganisms discussed herein or otherwise known in the art to assist with helical folding. As used herein a "coiled-coil forming sequence" is a peptide domain having a gently twisted, rope like bundle such as that disclosed in K. Reid et al (1994) FEBS Lett. May 16; 344(2-3):191-5 and as reviewed in Muller et al (2000) Meth. Enzymol. 328:261-283. Coiled coil sequences are comprised of a seven-residue repeat with positions 1-4 commonly being occupied by one or more hydrophobic amino acids and the remaining three amino acids being comprised of, generally, polar amino acids. Examples of coiled-coil sequences include, but are not limited to coiled-coil neck domains of collecting family proteins, a triple alpha-helical coiled-coil domain from human mannose-binding lectin, or coiled-coil domains from other collagen types, including bacterial collagens.

As used herein the term "foldon" refers to an amino acid sequence that is also sufficient to drive the multimerization and/or correct folding of a collagen domain (e.g. S Frank et al (2001) J. Mol. Biol. 308:1081-1089. Examples of foldon domains include a bacteriophage T4 fibritin foldon domain.

Addition of Moieties

The desired biological functionality of the collagen-like protein may be facilitated by the addition of one or more moieties. Examples of such moieties include, but are not limited to peptides, carbohydrates, small molecules, drugs, antibodies, PEG-based compounds, toxins, dyes, imaging agents or binding sequences.

Inserts

The recombinant collagen-like protein of the present disclosure may be engineered to include an insert sequence which provides a desired biological functionality. In one example, the insert sequence facilitates binding of the collagen-like protein to a targeted cell type or provides a natural cleavage sited for degradation in the body. Binding sequences include for example, integrin binding domains such as those identified for α2β1 integrin or an α3β1. Other sequences include the known type II collagen binding site for DDR2.

Cleavage sequences may include, but are not limited to, one or more sequences within the family of Matrix Metalloproteinase (MMP) domains, e.g. MMP-1, MMP-2, MMP-8, MMP-13 and MMP-18 which cleave type I, II and III collagens and MMP-2 and MP-9 which cleave denatured collagens.

Uses of the Collagen-Like Proteins of the Present Disclosure

For medical applications, collagen is generally used in two distinct formats. In one, intact tissue is used after further chemical stabilisation. The other, which is the format used in the present disclosure, is through preparation of purified soluble collagen which can be reconstituted into various products, such as dry, stabilised sheets or extruded fibres useful for wound dressings, adhesion barriers or devices for meniscal repair, with the processing giving the desired shape or form for the product. If necessary, the collagen-like protein material(s) can be stabilised, either by chemical fixation, e.g., glutaraldehyde, or by a physical method e.g., dehydrothermal cross-linking. Purified soluble collagen has also been used extensively as a collagen paste for soft tissue augmentation and also for treatment of urinary incontinence. Reconstituted products are characterised by a high biochemical purity associated with low immunogenicity, controlled turnover, often over short time periods, controlled porosity and retention of cell-matrix interactions that are important in biological functions in tissues.

The collagen-like proteins of the present disclosure may be utilized in various applications and procedures including, but not limited to, soluble recombinant collagens, such as use in dental implants, drug carriers, plastic coatings or medical devices, implant coatings, shape-formation materials, viscosurgery, vascular sealants, cosmetics and regulators of enzyme activity (e.g. metalloproteinases); sponge-like materials such as for use in three-dimensional cell cultures, tissue and organ engineering, hemostatic agents; gel-like materials, such as for use in tissue implants, corneal shields, contact lenses, and matrices for cell culture; and membrane-like materials, such as for use in anti-adhesion membranes, drug delivery systems, artificial skin and the like.

The collagen-like proteins of the present disclosure can be used in tissue engineering or other manufactured products based on collagen.

For example, the collagen-like proteins can be used in osteogenic and chondrogenic procedures, cartilage reconstruction, bone graft substitutes, hemostasis, wound treatment and management, reinforcement and support of tissues, incontinence etc.

Additionally, the collagen-like proteins of the present disclosure can be used outside of the biomedical arena with industrial applications including, but not limited to stabilizers, thickeners in glue manufacture, emulsifiers, foaming agents suitable for paper or textile manufacture, photographic films, manufacture of rubber substitutes, food industry applications, and the like.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

EXAMPLES

Example 1

A Bacterial Collagen Sequence with an Introduced Tyr Residue at the C-Terminal

The DNA sequence for the fragment of the scl2.28 allele (Q8RLX7) encoding the combined globular and collagen-like portions of the Scl2.28 protein, but lacking the C-terminal attachment domain, was obtained from the data provided in the National Center for Biotechnology Information database (National institutes of Health, Bethesda, Md. 20894, USA) as record GenBank: AY069936.1). To this sequence a His$_6$ tag was introduced at the N-terminal and a thrombin/trypsin cleavage sequence LVPRGSP (SEQ ID NO: 1) was inserted between the N-terminal globular domain (V) and the following (Gly-Xaa-Yaa)$_n$ triple-helical/collagen-like (CL) domain sequence. A triplet sequence GKY was included at the C terminal of the CL domain, followed by a stop codon, with NdeI and BamHI cloning sites. The DNA for this design was synthesised commercially without any codon optimisation. SEQ ID NO: 2 is the final DNA construct. SEQ ID NO:3 is the translated protein sequence.

Example 2

A Bacterial Collagen Sequence with an Introduced Cys Residue at the N-Terminal

The DNA sequence for the triple helix repeat-containing collagen from Candidatus Solibacter usitatus Ellin6076 is obtained from the data provided in the National Center for Biotechnology Information database (National institutes of Health, Bethesda, Md. 20894, USA) as record ABJ82342. The DNA sequence for the V-domain from Rhodopseudomonas palustris was obtained from the data provided in the National Center for Biotechnology Information database (National institutes of Health, Bethesda, Md. 20894, USA) as YP_001993084. The protein sequences are translated into nominal DNA sequences and a composite gene designed that maintains the correct coding framework, with a Met initiation signal followed by an extra amino acid sequence that contained a Cys residue, Gly-Cys-Pro, then the CL domain from S. usitatus, then the V-domain from R. palustris, followed finally by a C-terminal His$_6$-tag and a termination codon. Terminal restriction sites outside the coding sequence are added as NdeI and EcoRI for 5' and were SaiI and HindIII for 3'. This construct was synthesised commercially with a DNA sequence that retained the original amino acid sequence while optimising for expression in a desired host system, E coli. The final sequence construct is described in SEQ ID NOs:4 and 5.

Example 3

A Bacterial Collagen Sequence with Introduced Cys and Tyr Residues Both at the C Terminal The sequence of this example was prepared as described in Example 1, except that the sequence at the C-terminal of the protein, at the end of the CL-domain was Gly-Tyr-Cys, followed by a stop codon and restriction sites, with the DNA for this sequence synthesised commercially without any codon optimisation. The sequence of this construct is shown in SEQ ID NOs:6 and 7.

Example 4

A Bacterial Collagen Sequence with Introduced Tyr and Cys Residues, Both at the C-Terminal The sequence of this example was prepared as described for Example 1, except that the sequence lacks the thrombin/trypsin-like cleavage site prior to the N-terminal of the CL domain. At the C-terminal of the protein, at the end of the CL-domain was added GlyCysCysGlyLysTyr (SEQ ID NO:8), followed by a stop codon and restriction sites, with the DNA for this sequence synthesised commercially without any codon optimisation. The sequence of this construct is shown in SEQ ID NOs:9 and 10.

Example 5

A Bacterial Collagen Sequence with Introduced Tyr and Cys Residues, at the N- (Cys) and C- (Tyr-Cys) Terminals The sequence of this example was prepared as described for Example 1, except that the sequence between the V-domain and the CL-domain contains an extra Gly-Cys-Pro triplet. At the C-terminal of the protein, at the end of the CL-domain is Gly-Tyr-Cys, followed by a stop codon and restriction sites. The DNA for this sequence is synthesised commercially without any codon optimisation. The sequence of this construct is shown in SEQ ID NOs:11 and 12.

Example 6

A Bacterial Collagen Sequence with Introduced Tyr Residues at the N- and C-Terminals The sequence of this example was prepared as described for Example 1, except that the sequence between the V-domain and the CL-domain contains an extra Gly-Tyr-Pro triplet. At the C-terminal of the protein, the end of the CL-domain is Gly-Lys-Tyr, followed by a stop codon and restriction sites. The DNA for this sequence was synthesised commercially without any codon optimisation. The sequence of this construct is shown in SEQ ID NOs:13 and 14.

Example 7

A Bacterial Collagen Sequence with an Introduced Tyr Residue within the tripl-Helical/Collagen-Like Domain The sequence of this example was prepared as described for Example 2, except that the CL sequence contains an N-terminal GlyProPro sequence rather than a GlyCysPro sequence and also contained an inserted (substituted) integrin binding sequence, GlyGluArgGlyPheProGlyGluArg-GlyValGlu (SEQ ID NO:15), and an extra (substituted) Gly-Tyr-Pro triplet. This construct is synthesised commercially with a DNA sequence that retains the original amino acid sequence while optimising for expression in a desired host system, *E coli*. The final sequence construct is described in SEQ ID NOs:16 and 17.

Example 8

A Bacterial Collagen Sequence with an Introduced Cys Residue within the Triple-Helical/Collagen-Like Domain The sequence of this example was prepared as described for Example 6, where the CL sequence contains an inserted (substituted) integrin binding sequence, but in this example an extra (substituted) Gly-Cys-Pro triplet rather than a Tyr containing triplet. This construct was synthesised commercially with a DNA sequence that retains the original amino acid sequence while optimising for expression in a desired host system, *E coli*. The final sequence construct is described in SEQ ID NOs:18 and 19.

Example 9

A Bacterial Collagen Sequence with Introduced Tyr and Cys Residues within the Collagen-Like/Triple-Helical Domain The sequence of this example is prepared as for Example 6 and Example 7, where the CL sequence contains an inserted (substituted) integrin binding sequence, but in this example contains both an extra (substituted) Gly-Cys-Pro triplet as well as an extra (substituted) Gly-Tyr-Pro triplet. The construct is synthesised commercially with a DNA sequence that retains the original amino acid sequence while optimising for expression in a desired host system, *E coli*. The final sequence construct is described in SEQ ID Nos:20 and 21.

Example 10

Transformation, Expression, Extraction, and Purification of Recombinant Collagen-Like Proteins Any one of the DNA constructs, as described in Examples 1-9 with SEQ ID Nos: 2-19 can be cloned into *E. coli* and be made to express triple-helical protein. The DNA sequence according to Example 5 was sub-cloned into the *E. coli* expression vector system pCold using the unique sites 5' NdeI and 3' BamHI. The PCR colony screening technique was then used to detect positive clones. These clones were grown up in 100 ml culture volumes and Qiagen midi preps carried out to expand the vector quantity. For expression, a selected positive clone was transformed into the *E. coli* host BL21-DE3. Cells were grown in 2×YT Media (or Defined media could also be used) with ampicillin (50 µg/ml) at 37° C. for 24 h and cell culture optical density at A600 reached around 3-6. The culture was then incubated at 25° C. and 1 mM isopropyl beta-D-thiogalactopyranoside added to induce protein expression. After 10 h incubation at 25° C., the temperature was decreased to 15° C. for another 14 h incubation. After 24 h incubation, cells were harvested by centrifugation.

Alternatively, the DNA sequence according to the Examples can be sub-cloned into the *E. coli* expression vector pET21a using 5' EcoRI and 3' HindIII sites. Transformed cells were plated onto YT plus Ampicillin plates and grown overnight at 37° C. A single colony was picked from this plate and grown overnight in YT plus Ampicillin media at 37° C. Samples were diluted 1:1 with fresh medium and induced with 1 mM isopropyl beta-D-thiogalactopyranoside and growth continued for a further 4 h under the same conditions. Cells were then harvested by centrifugation.

For extraction, each 1 gram of cell paste, derived as above, was resuspended in 20 ml of 50 mM acetic acid/HCl buffer pH2, and the cells burst by sonication, using a Misonix S4000 instrument, with a Enhance Booster #1 probe, at 30 A (instrument scale) for 5 minutes. The cell lysate mixture was clarified by centrifugation (20,000×g for 40 min) and the clear supernatant containing the triple helical protein was retained. The presence of soluble triple helical protein after expression and extraction was confirmed by SDS-PAGE.

For protein samples that had an attached $His_6$ tag, either included in the sequence or included by the vector, clarified supernatant was taken to 20 mM sodium phosphate 150 mM NaCl and 50 mM imidazole buffer, pH8.5, and absorbed onto a Ni charged HyperCel-Sepharose metal ion affinity resin (Pall Life Sciences). Elution was by the same buffer, but containing 500 mM imidazole.

Alternatively, extracted protein after clarification, was adjusted to pH 2.2 and left for 16 h to allow precipitation. The sample was then centrifuged for 30 min and 12,000×g and the supernatant, containing the triple-helical protein, retained. The supernatant obtained after removal of acid precipitated proteins was adjusted to pH 2.5 and pepsin (0.01 mg/ml) added and proteolysis allowed to proceed for 16 h at 4° C.

Fractions containing recombinant triple-helical protein after removal of impurities by use of affinity chromatography or by acid precipitation followed by protease treatment, as above discussed in previous examples, were pooled and then concentrated and exchanged into 20 mM sodium phosphate buffer, pH8.0, using a 10 kDa cross-flow filtration membrane apparatus (Pall Life Sciences). Optionally, after adjusting to pH 8.0, a second digest with trypsin added to 0.01 mg/ml was performed for 16 h at 4° C.

Optionally, further purification is achieved on a Sephacryl S200 26/60 column (GE Healthcare).

All extraction and purification steps were performed at temperatures less than the melting temperature of the triple helix, preferably at 4° C.

Example 11

Figure 3:
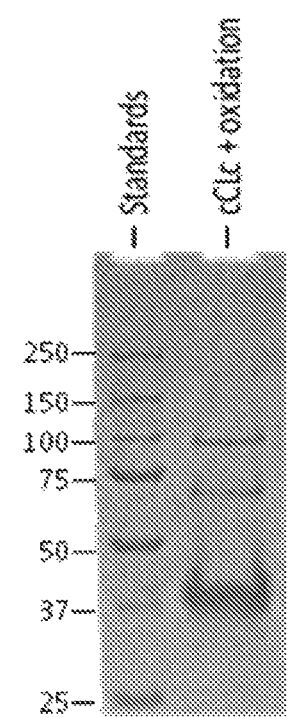
FIG. 3 shows SDS PAGE of molecular weight standards (left lane) and a purified, modified bacterial (S. pyogenes) collagen domain protein with introduced Tyr and Cys residues at the N- (Cys) and C- (Tyr-Cys) terminals (right hand lane) after cross-linking by brief (30 min) oxidation by bubbling through air. This shows the band of the starting material (highest mobility band, furthest from the gel pocket) and a range of higher molecular weight bands (slower moving, nearer the gel pocket) that have arisen from the oxidative crosslinking between Cys residues to give dimers, trimers, tetramers, etc.

Direct Crosslinking of Modified Bacterial Collagen-Like Sequences Through Formation of Disulfide Bonds Between Cys Residues A solution of purified protein, containing introduced Cys residues as described in Example 5 (with a Cys at the N-terminus and C-terminus) was adjusted to pH 7.2 in 20 mM sodium phosphate buffer, 0.15 M NaCl. Air was bubbled though the solution for 30 mins, with the volume topped up with water as needed to maintain the initial volume, or alternatively, the sample was allowed to stand in air for >4 days to facilitate cross-linking. FIG. 3 shows a SDS-PAGE gel demonstrating cross-linking of the protein as shown by the higher molecular weight band compared with the single band of the starting material.

Example 12

Figure 4:
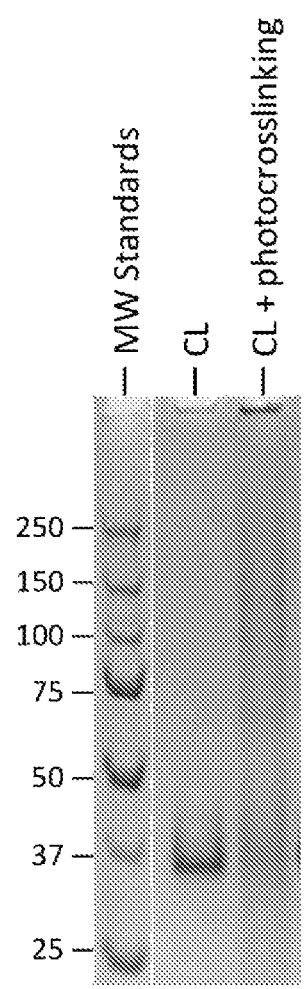
FIG. 4 shows SDS PAGE of molecular weight standards (left lane) and a purified, modified bacterial collagen protein, being a S. pyogenes CL domain with a Tyr residue at C-terminus (centre lane) after cross-linking by photo-cross-linking (right hand lane) using 2 mM [Ru$^{II}$(bpy)$_3$]Cl$_2$ and 10 mM sodium persulfate in PBS and irradiation for 20 sec at a distance of 20 mm with a LED dental curing lamp (430-480 nm, peak wavelength 455 nm±10 nm, 1200 mW/cm$^2$ at source, 3M ESPE™ S10 LED curing Light). After photo-crosslinking, the protein molecular weight had increased such that most of the sample no longer entered the gel, and faint bands of dimers, trimers, etc. were present.

Direct Crosslinking of Modified Bacterial Collagen-Like Sequences Through Formation of Dityrosine Bonds by Photo-Crosslinking A solution of purified protein, containing introduced Tyr residues as described in Example 1 was adjusted to pH 7.2 in 20 mM sodium phosphate buffer, 0.15 M NaCl and 2 mM [Ru$^{II}$(bpy)$_3$]Cl$_2$ and 10 mM sodium persulfate (SPS) added. Crosslinking was performed by irradiation for 3 times at 20 sec at a distance of 10-15 mm with a LED dental curing lamp (430-480 nm, peak wavelength 455 nm±10 nm, 1200 mW/cm$^2$ at source, 3M ESPE™ S10 LED curing Light). The cross-linked protein is recovered by dialysis against 20 mM acetic acid and freeze drying. FIG. 4 shows the SDS-PAGE gel.

Example 13

Figure 5:
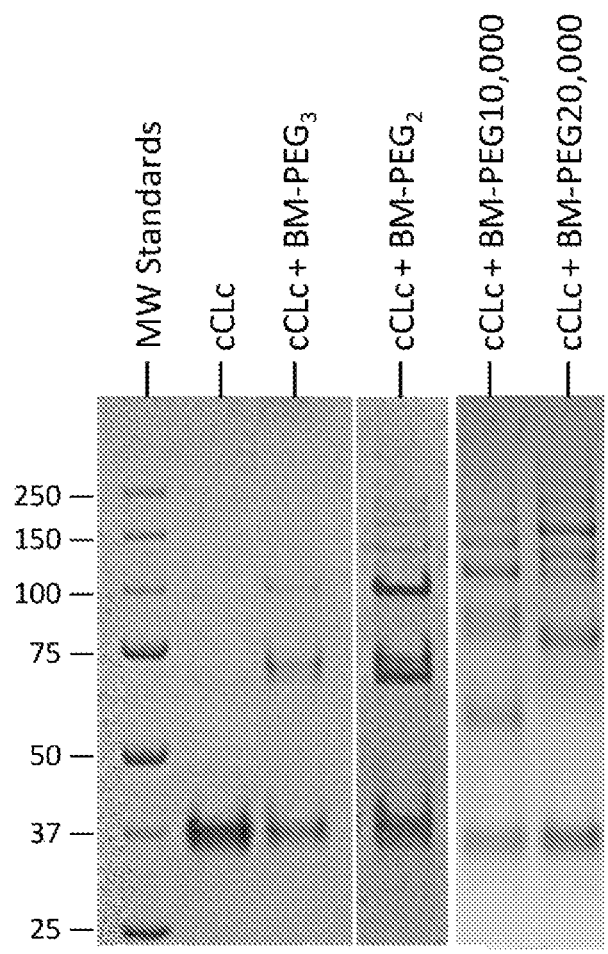
FIG. 5 shows SDS PAGE of molecular weight standards (left panel, lane 1) and a purified, modified bacterial (S. pyogenes) collagen domain protein with introduced Tyr and Cys residues at the N- (Cys) and C- (Tyr-Cys) terminals (left panel, lane 2), after cross-linking by addition of a 3 fold molar excess of either bis-maleimidyl-PEG3 (left panel, lane 3), bis-maleimidyl-PEG$_2$ (centre panel, lane 4), bis-maleimidyl-PEG10,000 (right panel, lane 5) or bis-maleimidyl-PEG20,000 (right panel, lane 6) showing the formation of crosslinked higher molecular weight dimers, trimers and polymers of the protein.

Crosslinking of Modified Collagen-Like Bacterial Sequences Through Reaction with Site Specific Bifunctional Reagents—Bis-Maleimidyl PEGs Reacting with Cys Residues A solution of purified protein, containing introduced Cys residues as described in Example 5 was reduced by adding 3-4 equivalents of tris(carboxyethyl)phosphine (Pierce) and adjusted to pH 6.8 in 20 mM sodium phosphate buffer, 0.15 M NaCl and 10 mM EDTA. Protein was reacted with either bis maleimidyl (PEG)$_2$ (Pierce), bis maleimidyl (PEG)$_3$ (Pierce) bis maleimidyl (PEG-10,000) (Sunbright DE100MA; NOF Corporation) or bis maleimidyl (PEG-20,000) (Sunbright DE200MA; NOF Corporation). The reaction was allowed to proceed for 2 hr. The cross-linked protein was recovered by dialysis and freeze drying. FIG. 5 shows the SDS-PAGE gel demonstrating higher molecular weight bands arising from modification and cross-linking.

Example 14

Figure 6:
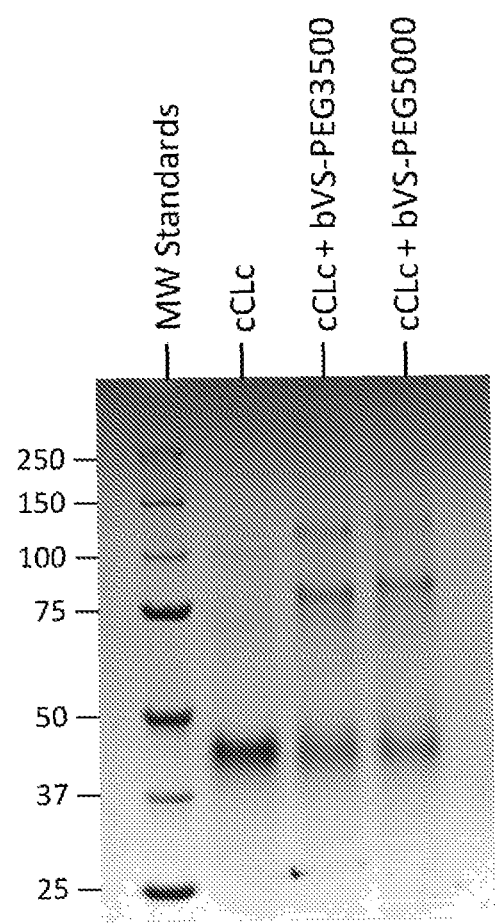
FIG. 6 shows SDS PAGE of molecular weight standards (left, lane 1) and a purified, modified bacterial (S. pyogenes) collagen domain protein with introduced Tyr and Cys residues at the N- (Cys) and C- (Tyr-Cys) terminals (lane 2), after reaction with bis vinyl sulfone PEG3500 (lane 3) and with bis vinyl sulfone PEG5000 (lane 4), showing dimers, trimers and polymers of protein.

Crosslinking of Modified Bacterial Collagen-Like Sequences Through Reaction with Site Specific Bifunctional Reagents—Bis-Vinylsulfone PEG Reacting with Cys Residues A solution of purified protein, containing introduced Cys residues as described in Example 5 was adjusted to pH 8.0 in 20 mM sodium phosphate buffer, 0.15 M NaCl. Protein was reduced by adding 3-4 equivalents of tris(2-carboxyethyl)phosphine (Pierce). The protein was then reacted with a 2 fold molar excess of either di-vinylsulfone PEG (MW 3500) (JenKem Technology) or di-vinylsulfone PEG (MW 5000) (JenKem Technology) for 16 hr reaction time. The cross-linked protein was recovered by dialysis and freeze drying. FIG. 6 shows the SDS-PAGE gel demonstrating higher molecule weight bands arising from modification and cross-linking.

Example 15

Modification of Bacterial Collagen-Like Sequences Through Reaction with Site Specific Chemical Entity—a Maleimidyl Peptide Sequence Reacting with Cys Residues In some cases, the purification method used may remove a sequence tag, such as a His$_6$ tag that can be useful in tracking the bacterial collagen. In such a case a tag can be re-introduced. Alternatively, an amino acid or peptide sequence not readily incorporated by recombinant technology, such as a cyclic peptide, or one including a D-amino acid, or one including a modified or non-natural amino acid can be introduced. The modification described in this Example used FLAG peptide (Sigma) which was reacted at a 5-fold excess with NHS-maleimidyl (PEG)$_2$ (Thermo) at low pH, pH 6.8 sodium phosphate, to preference reaction with the N-terminal α-amino group.

Figure 7:
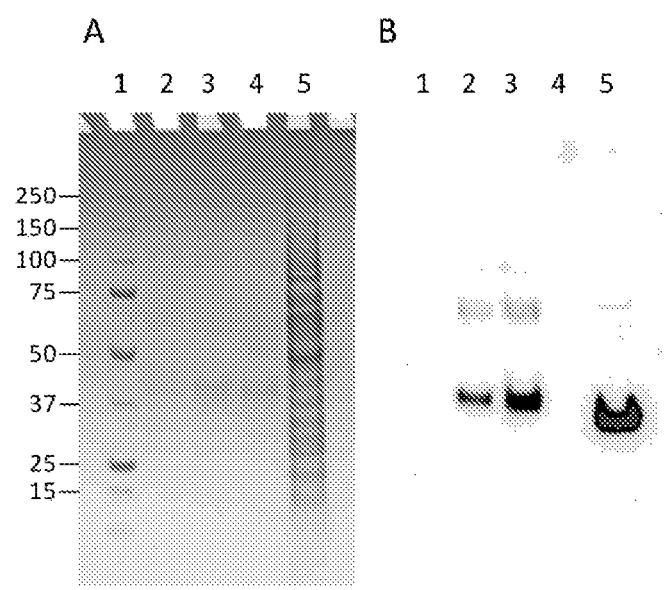
FIG. 7 shows (A) Coomassie blue stained SDS PAGE and (B) a Western blot, stained with anti-Flag antibody. Samples are: molecular weight standards (lane 1), a purified, modified bacterial (S. pyogenes) collagen domain protein with a introduced Cys residues at N- and C-terminals, further modified to introduce a FLAG peptide (lane 2 and lane 3 double loading), the same protein, but without addition of the FLAG peptide (lane 4) and a positive control recombinant protein extract containing a FLAG modified protein.

A solution of purified protein described in Example 5 was adjusted to pH 7.4 in 20 mM sodium phosphate buffer, 0.15 M NaCl and reacted for 2 h with the maleimidyl PEG (MW 2000)-FLAG peptide conjugate described above. If required, prior reduction of the protein to eliminate disulphide bonds can be performed with 5 mM tris(2-carboxyethyl)phosphine (TCEP). The modified protein was recovered by dialysis and freeze drying. FLAG peptide addition was shown by SDS-PAGE followed by Western blotting with an anti-FLAG antibody as shown in FIG. 7.

Example 16

Modification of Bacterial Collagen-Like Sequences Through Reaction with Site Specific Chemical Entity—a Bromoacetyl Peptide Sequence Reacting with Cys Residues A solution of purified protein, containing introduced Cys residues described in Example 5 was adjusted to pH 7.2 in 20 mM sodium phosphate buffer, 0.15 M NaCl and was then reacted with either bromoacetyl-Gly-Arg-Arg-Arg (SEQ ID NO: 24) or bromoacetyl-Gly-Arg-Gly-Asp-Ser (SEQ ID NO: 25). The modified proteins were recovered by dialysis and freeze drying. The reaction with bromoacetyl-Gly-Arg-Arg-Arg (SEQ ID NO: 24) was assessed by increased binding of fluorescein isothiocyanate labelled heparin (Molecular Probes). Modified protein and control (unmodified)

samples were coated onto a tissue culture plastic plates and left overnight at 4° C. Samples were washed 3 times with 3% BSA and then held with 3% BSA at RT for 5 hr. FITC Heparin was added and incubated for >4 h at 4° C. in the dark. After extensive washing with PBS, the fluorescence was examined with a plate reader (PHERAstar). This showed that fluorescent intensity increased in comparison to the control cCLc sample where no peptide was added. The reaction with bromoacetyl-Gly-Arg-Gly-Asp-Ser (SEQ ID NO: 25) was monitored by the same method, or is shown by enhanced cell binding to the modified protein.

Example 17

Modification of Bacterial Collagen-Like Sequences Through Reaction with Site Specific Chemical Entity—a Tyrosine Containing Peptide Sequence Reacting with Tyr Residues A solution of purified protein, containing introduced Tyr residues as described in Examples 1, 3-7, and 9, is adjusted to pH 7.2 in 20 mM sodium phosphate buffer, 0.15 M NaCl and 2 mM [Ru$^{II}$(bpy)$_3$]Cl$_2$. 10 mM sodium persulfate (SPS) is added plus 10 mM Tyr-Arg-Arg-Arg. The reaction is carried out by irradiation for 3 times at 20 sec at a distance of 10-15 mm with a LED dental curing lamp (430-480 nm, peak wavelength 455 nm±10 nm, 1200 mW/cm$^2$ at source, 3M ESPE™ S10 LED curing Light). The modified protein is recovered by dialysis and freeze drying. The reaction is assessed by increased binding of fluorescein isothiocyanate labelled heparin (Molecular Probes) in the same buffer.

Example 18

Figure 8:
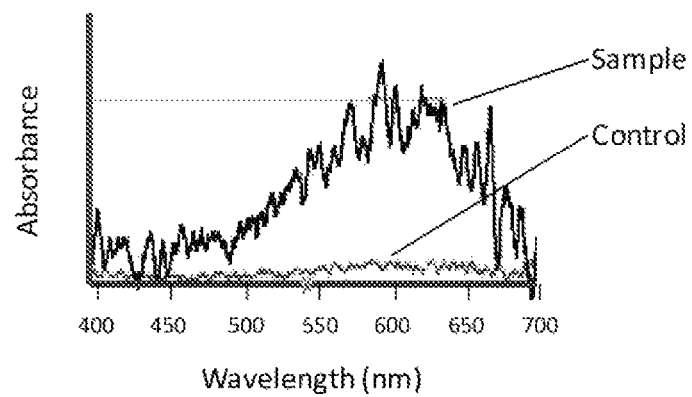
FIG. 8 shows the visible spectrum of modified bacterial (S. pyogenes) collagen domain protein with introduced Tyr and Cys residues at the N- (Cys) and C- (Tyr-Cys) terminals after reaction with a vinylsulfone labelled dye QXL 610 vinylsulfone (Anaspec) that reacts with Cys residues. The QXL 610 labelling is shown by the peak at 594 nm.

Modification of Bacterial Collagen-Like Sequences Through Reaction with Site Specific Chemical Entity—a Vinylsulfone Labelled Dye Reacting with Cys Residues A solution of purified protein, containing introduced Cys residues as described in Example 5 was adjusted to pH 8.0 in 20 mM sodium phosphate buffer, 0.15 M NaCl. Protein was reduced by adding 3-4 equivalents of tris(2-carboxyethyl)phosphine (Pierce). The protein was then reacted with a 2 fold molar excess of QXL 610 vinylsulfone (Anaspec), using a concentrated stock (15.6 mM) in dimethylsulfoxide. After 1 h reaction, excess dye was quenched with 10 mM DTT. Excess reagents were removed by gel filtration or by dialysis. The extent of QXL 610 labelling was determined at 594 nm using an extinction of 11,000 M$^{-1}$ cm$^{-1}$. The modified protein was recovered by dialysis and freeze drying. A spectrum as shown in FIG. 8 was recorded using a NanoDrop ND1000 Spectrophotometer.

Example 19

Modification of Bacterial Collagen-Like Sequences Through Reaction with Site Specific Chemical Entity—a Maleimidyl Labelled Sugar Reacting with Cys Residues Lactobionic acid (Sigma) was converted to an NHS derivative using M aqueous N-hydroxysuccinimide (NHS) and 1-ethyl-3-(3-dimethylaminopropyl) carbodiimide, HCl (EDC) (Sigma). This product is then reacted with maleimide-PEG-amine (MW 2000) TFA Salt (JenKem) at pH 6.8 in sodium carbonate. The maleimidyl-PEG-Sugar product is then reacted with a solution of purified protein, containing introduced Cys residues described in any of Examples 2-5, 8 and 9, adjusted to pH 7.4 in 20 mM sodium phosphate buffer. Protein is reduced by adding 3-4 equivalents of tris(2-carboxyethyl)phosphine (Pierce). The modified protein is recovered by dialysis and freeze drying.

Example 20

Modification of Bacterial Collagen-Like Sequences Through Reaction with Two Different Site Specific Chemical Entities.

A collagen modified by two separate reactions can be made, with one reaction going through an added Cys residue and the other reaction going through an added Tyr residue. A solution of purified protein, containing introduced Cys and Tyr residues such as that described according to any one of Examples 3-5 or 9 is adjusted to pH 7.2 in 20 mM sodium phosphate buffer, 0.15 M NaCl and reacted for 2 h with modified FLAG peptide (as in Example 15). If required, prior reduction of the protein to eliminate disulphide bonds can be performed with 5mM tris(2-carboxyethyl) phosphine (TCEP). The modified protein is recovered by dialysis to pH 7.2 in 20 mM sodium phosphate buffer, 0.15 M NaCl and is then reacted at the introduced Tyr residue with Tyr-Arg-Arg-Arg (SEQ ID NO: 26), through addition of 2 mM [Ru$^{II}$(bpy)$_3$]Cl$_2$ and 10 mM sodium persulfate (SPS) added plus 10 mM Tyr-Arg-Arg-Arg (SEQ ID NO: 26). The reaction is carried out by irradiation for 3 times at 20 sec at a distance of 10-15 mm with a LED dental curing lamp (430-480 nm, peak wavelength 455 nm ±10 nm, 1200 mW/cm$^2$ at source, 3 M ESPE™ S10 LED curing Light). The doubly modified protein is recovered by dialysis and freeze drying.

Example 21

Fabrication of Bacterial Collagen-Like Proteins of the Invention

A sponge may be prepared by freeze drying modified collagen prepared according to any Example described above and stabilising by dehydrothermal treatment under vacuum for 24 h at 110° C. This stabilisation approach gives a modified protein sponge that is stable at >37° C. Alternatively, glutaraldehyde vapour can be used for stabilisation according to standard methods. Alternatively, a collagen solution can be crosslinked, for example using glutaraldehyde, to provide a hydrogel that can then be freeze dried to form a sponge that is stable at >37° C.

The invention claimed is:

1. A collagen-like protein comprising one or more bacterial triple-helical domains having a GlyXaaYaa repeating motif, wherein at least one triple-helical domain is modified compared to a native bacterial triple-helical domain by the addition and/or substitution of one or more reactive amino acid residues at the N- and/or C-terminus of sad at least one triple helical domain, wherein:
   (i) the N-terminal residue and/or C-terminal residue of the at least one triple-helical domain is substituted with between 1 and 24 consecutive reactive amino acid residues, wherein the reactive amino acid residues are selected from Cys, Tyr, Trp, His, or combinations thereof;
   (ii) the N-terminal residue and/or C-terminal residue of the at least one triple-helical domain is substituted with between 1 and 15 GlyXaaYaa motifs and wherein either the Xaa or Yaa position of the motif(s) is a Cys or Tyr residue;
   (iii) between 1 and 15 GlyXaaYaa motifs are added to the N-terminal residue and/or C-terminal residue of the at least one triple-helical domain and wherein either the Xaa or Yaa position of the motif(s) is a Cys or Tyr residue; or
   (iv) the collagen-like protein comprises a combination of any one of or all of the amino acid additions and/or substitutions according to (i) to (iii).

2. The collagen-like protein according to claim 1, wherein between 1 and 10 reactive amino acid residues are added or substituted at the N-terminal and/or C-terminal of sad at least one triple helical domain.

3. The collagen-like protein according to claim 1, wherein the GlyXaaYaa repeating motif of the bacterial triple-helical domains is maintained.

4. The collagen-like protein according to claim 1, further comprising the addition and/or substitution of reactive amino acid residues between triple-helical domains.

5. The collagen-like protein according to claim 1 wherein the one or more triple-helical domains are joined by a spacer sequence selected from a thrombin/trypsin-like cleavage site, a heparin binding site, an integrin binding sequence, a cell surface receptor binding site, or combinations thereof.

6. The collagen-like protein according to claim 1 comprising two or more triple-helical domains of two or more different bacterial triple-helical proteins which are optionally separated by a linker, wherein the linker if present, maintains the triple-helical GlyXaaYaa repeating motif of bacterial triple-helical domains.

7. The collagen-like protein according to claim 1, wherein the substituted and/or added reactive amino acid residues are chemically reacted with an agent to provide a modified collagen-like protein with altered properties.

8. The collagen-like protein according to claim 7, wherein the chemical reaction:
   (i) induces cross-linking of the reactive amino acid residues; or
   (ii) provides for the attachment of a moiety to the reactive amino acid residues.

9. The collagen-like protein according to claim 8, wherein the moiety is selected from a peptide, carbohydrate, small molecule, drug, antibody, toxin, imaging agent, binding sequence and polyethylene glycol (PEG)-based compounds.

10. A biomaterial, cosmaceutical or therapeutic product comprising a collagen-like protein according to claim 1.

11. An artificial collagen-based material for use in non-medical application(s) comprising a collagen-like protein according to claim 1.

* * * * *

UNITED STATES PATENT AND TRADEMARK OFFICE
CERTIFICATE OF CORRECTION

| | |
|---|---|
| PATENT NO. | : 10,155,793 B2 |
| APPLICATION NO. | : 15/024290 |
| DATED | : December 18, 2018 |
| INVENTOR(S) | : John Alan Maurice Ramshaw et al. |

Page 1 of 1

It is certified that error appears in the above-identified patent and that said Letters Patent is hereby corrected as shown below:

In the Claims

In Claim 1 at Column 61, Line 7:
Delete "sad" and replace with --said--.

In Claim 2 at Column 61, Line 30:
Delete "sad" and replace with --said--.

Signed and Sealed this
Twenty-first Day of May, 2019

Andrei Iancu
*Director of the United States Patent and Trademark Office*